(12) United States Patent
Urisu et al.

(10) Patent No.: US 9,977,009 B2
(45) Date of Patent: May 22, 2018

(54) PLANAR PATCH CLAMP DEVICE AND PLANAR PATCH CLAMP SYSTEM

(71) Applicant: Japan Science and Technology Agency, Saitama (JP)

(72) Inventors: Tsuneo Urisu, Aichi (JP); Zhi-hong Wang, Aichi (JP); Hidetaka Uno, Aichi (JP); Yasutaka Nagaoka, Aichi (JP); Kei Kobayashi, Aichi (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days. days.

(21) Appl. No.: 14/915,560

(22) PCT Filed: Aug. 29, 2014

(86) PCT No.: PCT/JP2014/072808
§ 371 (c)(1),
(2) Date: Feb. 29, 2016

(87) PCT Pub. No.: WO2015/030201
PCT Pub. Date: Mar. 5, 2015

(65) Prior Publication Data
US 2016/0209395 A1 Jul. 21, 2016

(30) Foreign Application Priority Data
Aug. 30, 2013 (JP) .................................. 2013-180684

(51) Int. Cl.
*B01L 1/00* (2006.01)
*B01L 3/00* (2006.01)
(Continued)

(52) U.S. Cl.
CPC ..... *G01N 33/48728* (2013.01); *G01N 27/327* (2013.01); *G01N 27/3335* (2013.01); *G01N 2500/10* (2013.01)

(58) Field of Classification Search
CPC ..... C12M 23/40; C12M 35/02; B01L 3/5027; B01L 3/502715; B01L 3/502761; B01L 2300/0645
See application file for complete search history.

(56) References Cited

U.S. PATENT DOCUMENTS 6,315,940 B1 * 11/2001 Nisch ..................... C12M 23/12
204/403.01
6,846,668 B1 * 1/2005 Garman ................. C12M 35/00
435/285.1
(Continued)

FOREIGN PATENT DOCUMENTS

CN 102884427 A 1/2013
JP 2003-511668 A 3/2003
(Continued)

OTHER PUBLICATIONS

Urisu et al. Incubation type Si-based planar ion channel biosensor. Anal Bioanal Chem (2008), v391, p. 2703-2709.*
(Continued)

*Primary Examiner* — Nathan A Bowers
(74) *Attorney, Agent, or Firm* — Kilpatrick Townsend & Stockton LLP

(57) ABSTRACT

A planar patch clamp device comprising: an electrical insulating substrate (2) having a first surface having a cell arrangement region and a second surface of the opposite surface and having a through hole (3) in the cell arrangement region which does not pass cells, but pass liquid; a first reservoir (6) provided at the first surface side (2S) of the electrical insulating substrate (2) to be able to communicate with the through hole (3) and hold a first conductive liquid;
(Continued)

a first electrode part (7) arranged to be able to be electrically conductive with the first reservoir (6) through the first conductive liquid;

a second reservoir (6') provided at the second surface side (2S') of the electrical insulating substrate to be able to communicate with the through hole (3) and hold a second conductive liquid; a second electrode part (7') arranged to be able to be electrically conductive with the second reservoir (6') through the second conductive liquid; a supply path (8) connected to the second reservoir (6') and supplying the second conductive liquid to the second reservoir; a discharge path (9) connected to the second reservoir and discharging the second conductive liquid from the second reservoir (6'); and a valve (10) provided in the supply path and/or discharge path, able to allow or stop the flow of the second conductive liquid, and also able to allow or stop electrical conduction between the second reservoir (6') and the second electrode part (7').

9 Claims, 16 Drawing Sheets

(51) Int. Cl.
*C12M 1/00* (2006.01)
*G01N 33/487* (2006.01)
*G01N 27/327* (2006.01)
*G01N 27/333* (2006.01)

(56) References Cited

U.S. PATENT DOCUMENTS

| | | | | |
|---|---|---|---|---|
| 6,984,297 | B2* | 1/2006 | Nisch | G01N 33/48728 204/403.01 |
| 9,146,221 | B2* | 9/2015 | Guia | G01N 33/48728 |
| 2002/0182627 | A1* | 12/2002 | Wang | B01L 3/502761 435/6.11 |
| 2004/0168912 | A1* | 9/2004 | Klemic | G01N 33/48728 204/294 |
| 2005/0009004 | A1* | 1/2005 | Xu | G01N 33/48728 435/4 |
| 2011/0251102 | A1 | 10/2011 | Osipchuk et al. | |
| 2014/0339102 | A1* | 11/2014 | Urisu | G01N 27/416 205/792 |

FOREIGN PATENT DOCUMENTS

| | | |
|---|---|---|
| JP | 2005-536751 A | 12/2005 |
| JP | 2009-156572 A | 7/2009 |
| JP | 2009-204407 A | 9/2009 |
| WO | 01/25769 A2 | 4/2001 |
| WO | 2004/018690 A1 | 3/2004 |
| WO | 2014/045618 A1 | 3/2013 |
| WO | 2013/094418 A1 | 6/2013 |

OTHER PUBLICATIONS

English machine translation of JP 200904407 to Asano et al, generated 2017.*

Uno et al., "Development of neuronal network high throughput screening devices and application to disease model chip", the $61^{st}$ JSAP Autumn Meeting Koen Yokoshu, Mar. 3, 2014.

Uno et al., "Microfluidics control system of neuronal network high throughput screening device," $74^{th}$ JSAP Autumn Meeting Koen Yokoshu, Aug. 31, 2013.

Maltezos G., et al., "Design and fabrication of chemically robust three-dimensional microfluidic valves", Lab on a Chip, 2007, vol. 7, p. 1209-1211.

Roy E., et al., "Thermoplastic elastomers for microfluidics: Towards a high-throughput fabrication method of multilayered microfluidic devices", Lab on a Chip, 2011, vol. 11, pp. 3193-3196.

Unger M. A., et al., Monolithic Microfabricated Valves and Pumps by Multilayer Soft Lithography, Science, 2000, vol. 288, pp. 113-116.

Uno et al., "Development of neuronal network high throughput screening devices and application to disease model chip", the 61st JSAP Spring Meeting Koen Yokoshu, Mar. 3, 2014 19A-E15-3, <https://confit.atlas.jp/guide/event-img/jsap2014s/19a-E15-3/public/pdf?type=in>, retrieval date: Nov. 19, 2014.

Uno et al., "Microfluidics control system of neuronal network high throughput screening device", the 74th JSAP Autumn Meeting Koen Yokoshu, Aug. 31, 2013, 17A-C4-3, <https://confit.atlas.jp/guide/event-img/jsap2013a/17a-C4-3/public/pdf?type=in>, retrieval date: Nov. 19, 2014.

Urisu T., et al., "Incubation type Si-based planar Ion channel biosensor", Anal. Bioanal. Chem., 2008, vol. 391, pp. 2703-2709, Abstract.

PCT/JP2014/072808, Translation of International Search Report, dated Mar. 5, 2015, 2 pages.

Cheung et al., "Individually Addressable Planar patch Clamp Array," $2^{nd}$ Annual International IEEE-EMBS Special Topic Conference on Microtechnologies in Medicine & Biology, May 2-4, 2002, Madison, Wisconsin, p. 71-72.

Li, X., "Microfluidic System for Planar Patch-Clamp Electrode Arrays," a Dissertation Presented to the Faculty of the Graduate School of Yale University in Candidacy for the Degree of Doctor of Philosophy, 2006, 102 pages.

Li et al., "Microfluidic System for Planar Patch Clamp Electrode Arrays," Nano Letters, 2006, vol. 6, No. 4, pp. 815-819.

* cited by examiner

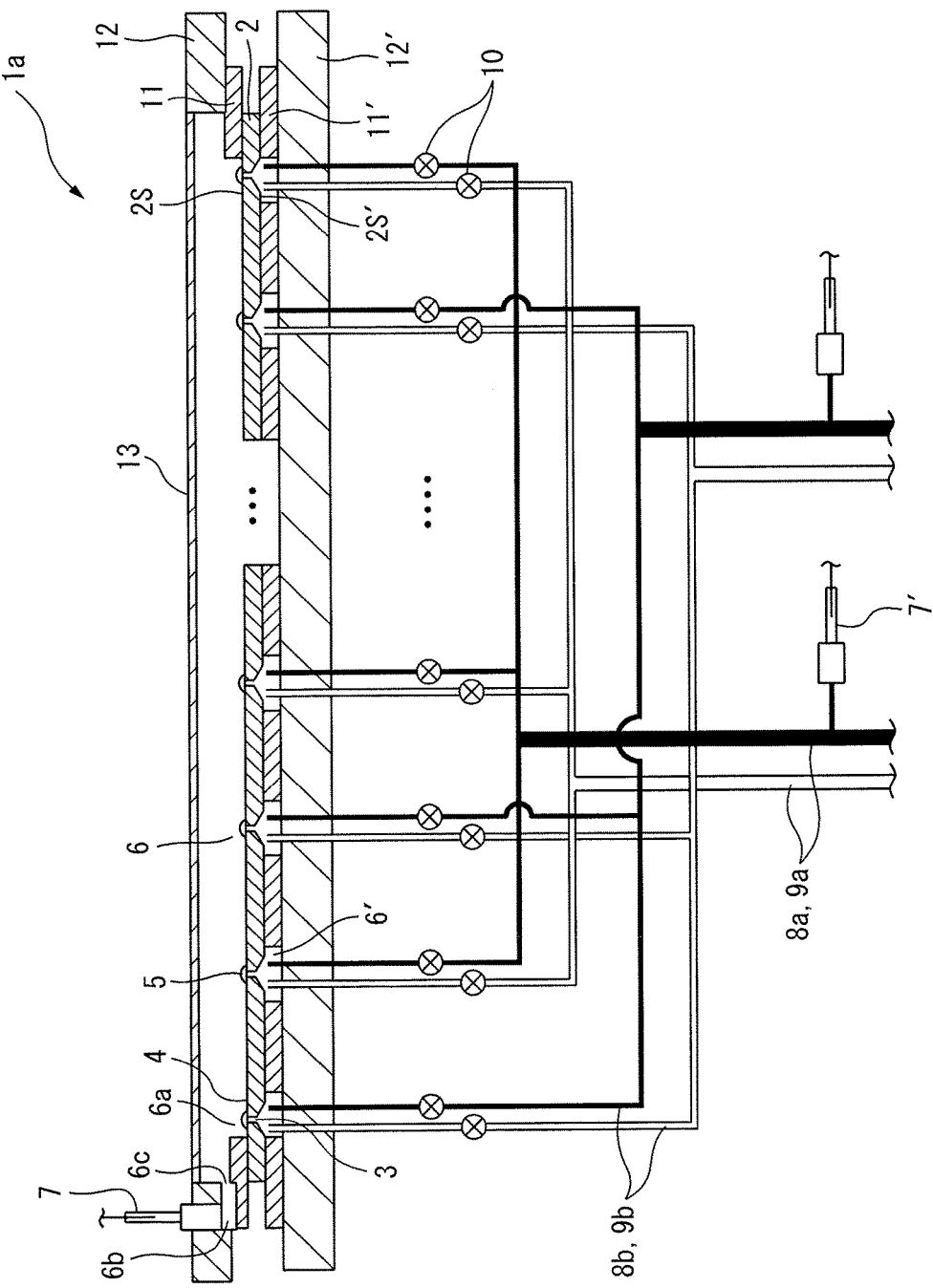

FIG. 8
(a)
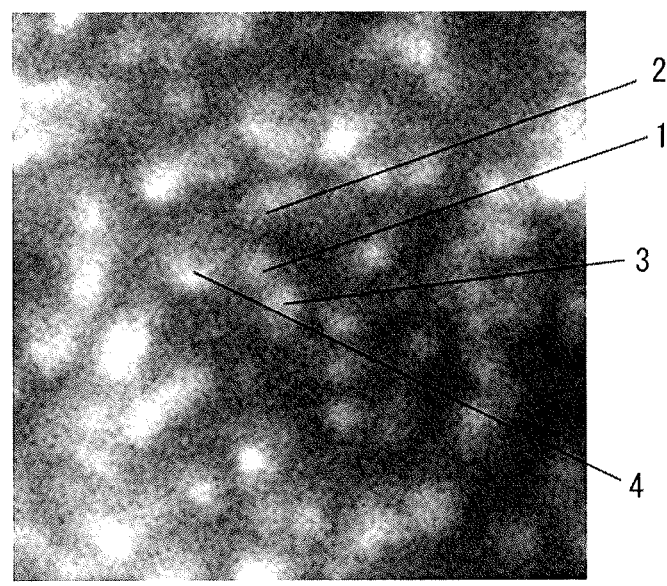
(b)
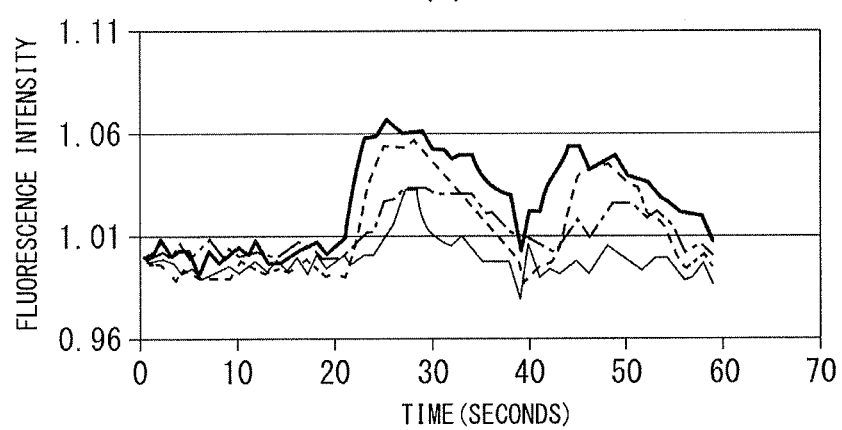

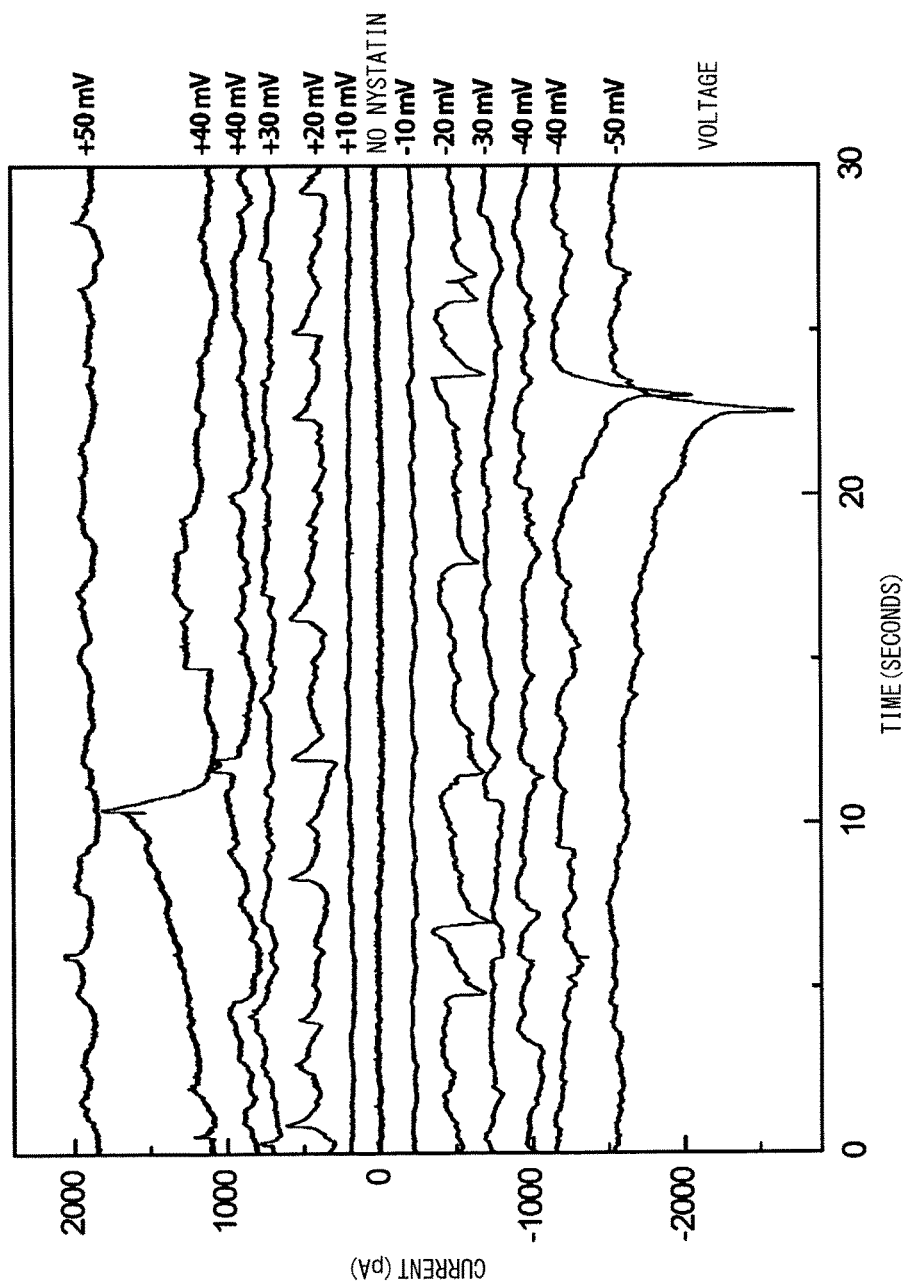

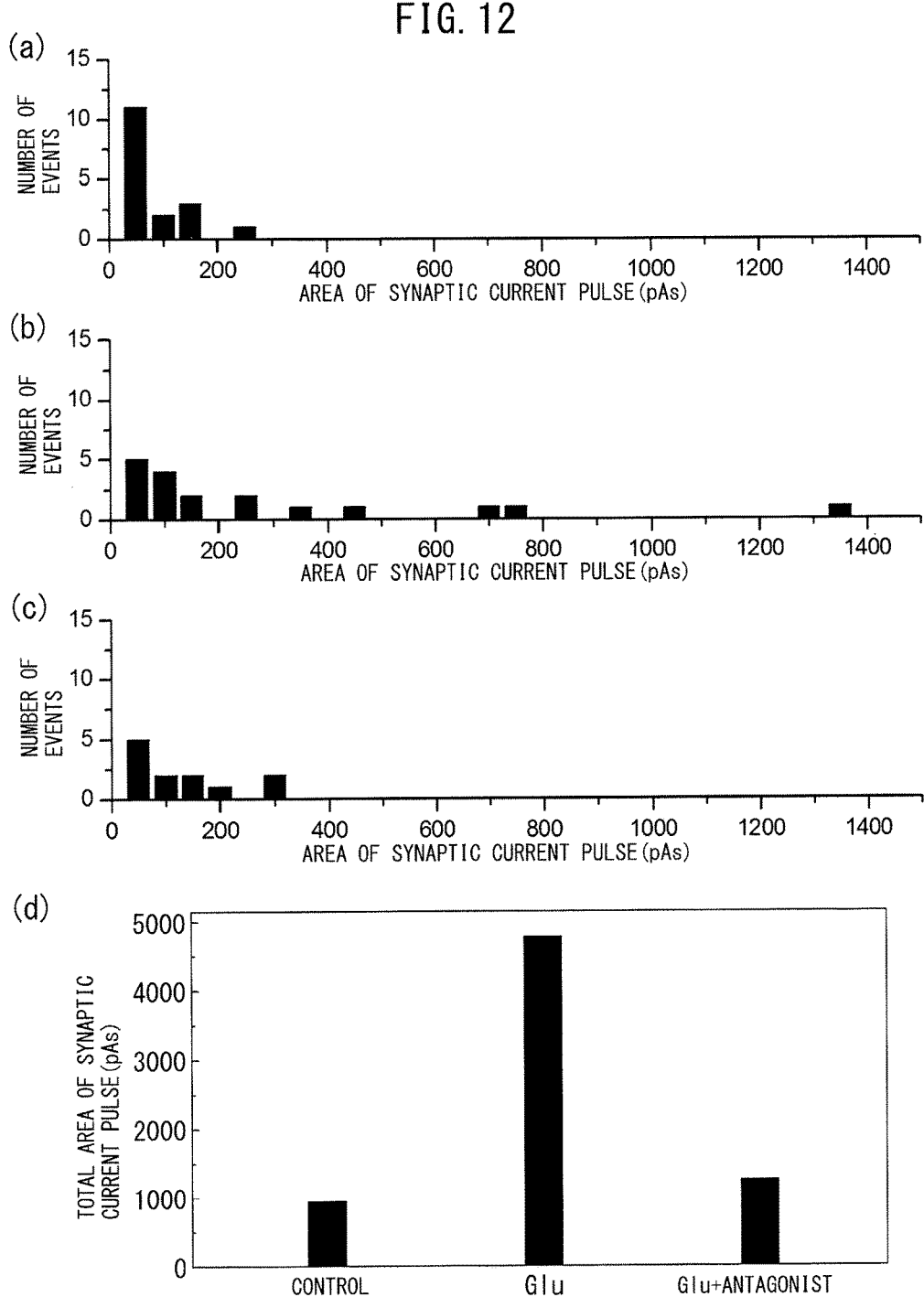

FIG. 13
(a)
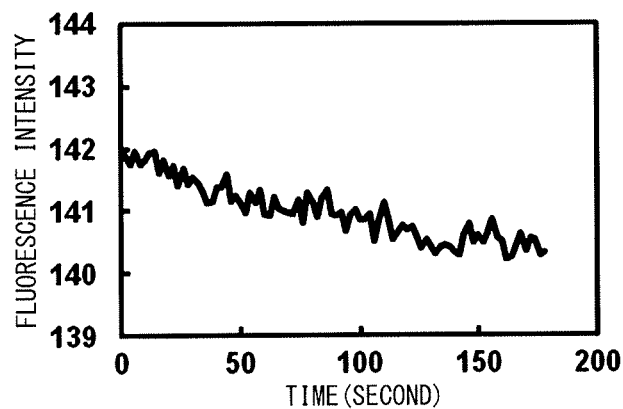
(b)
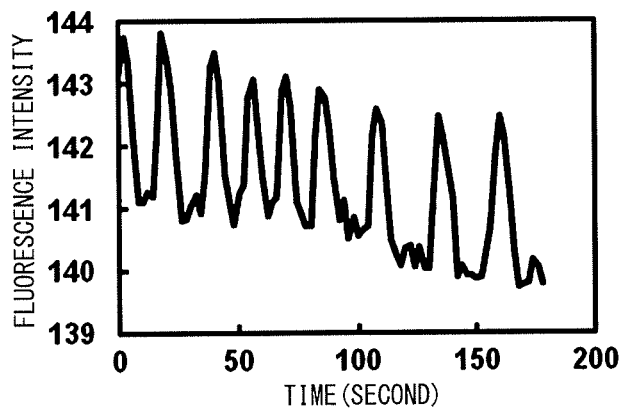
(c)
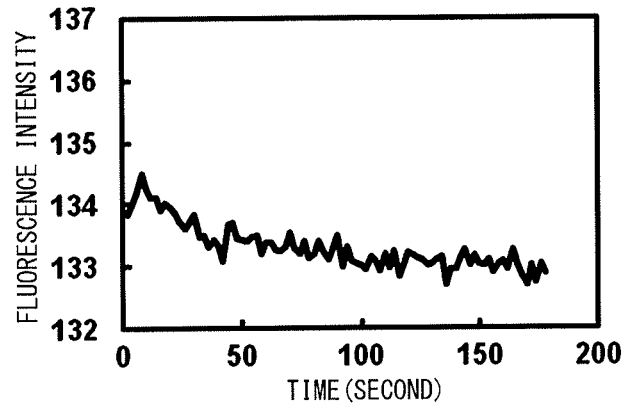

PLANAR PATCH CLAMP DEVICE AND PLANAR PATCH CLAMP SYSTEM

TECHNICAL FIELD

The present invention relates to a planar patch clamp device and planar patch clamp system measuring a current etc., accompanying electrical activity of a cell membrane. Further, it relates to a screening method of drugs using a planar patch clamp device or planar patch clamp system.

BACKGROUND ART

The membrane protein embedded in a cell membrane, called an "ion channel", is an important protein relating to the signal transmission in a biological system. In measurement of the function of an ion channel and drug development using this function, measurement of the current flowing through the ion channel is sought. In response to this demand, the patch clamp method was developed as art for measuring the ion channel current was.

The pipet patch clamp method was first developed as the patch clamp method, but there was the problem that the ion channel current of cells could only be recorded at a single point and therefore application to high throughput screening by multipoint measurement was not possible. As art for solving this problem, the planar patch clamp method was developed. The planar patch clamp method, for example, as disclosed in Japanese Patent Publication No. 2003-511668A (PLT 1), Japanese Patent Publication No. 2005-536751A (PLT 2), etc., provides a plurality of fine through holes in a silicon chip or other solid substrate, places cells on the individual through holes, and uses electrodes to measure the ion channel currents of the cells thereby enables measurement of the ion channel currents at multiple points. Specifically, the ion channel currents are measured by placing a bath solution around the cells on the substrate and a pipette solution at the lower side of the through holes of the substrate, placing electrodes (upper electrode and lower electrode) electrically conductive with the bath solution and pipette solution, respectively, and applying membrane potential between the electrodes.

The inventors have proposed various improvements to the planar patch clamp method up to now. For example, Japanese Patent Publication No. 2009-204407A (PLT 3) and Urisu et al., Analytical and Bioanalytical Chemistry, (2008), 391: 2703-2709 (NPLT 1) disclose a culture type planar patch clamp device setting an extracellular matrix-forming substance at the rims of the through holes of the substrate so as to extend the lifetimes of the cells arranged at the opening parts of the through holes and culturing the cells while measuring the ion channel currents. The pamphlet of International Patent Publication No. 2013/094418 (PLT 4) discloses a planar patch clamp device using electrode parts obtained by making the electrode container ends out of an inorganic porous material and sealing in a saturated electrode solution (salt bridge type electrode parts) to prevent fluctuations in membrane voltage, reduce noise, and improve the precision of current measurement. International Patent Publication No. PCT/JP2013/57976 (WO2014/045618: PLT 5) describes forming cell fixing locations surrounded by protrusions at a cell arrangement region including through holes on a cell culture substrate, thereby limiting the movement of nerve cells while forming a nerve cell network and improve the precision of current measurement.

CITATION LIST

Patent Literature

PLT 1. Japanese Patent Publication No. 2003-511668A
PLT 2. Japanese Patent Publication No. 2005-536751A
PLT 3. Japanese Patent Publication No. 2009-204407A
PLT 4. International Publication No. 2013/094418A
PLT 5. International Publication No. 2014/045618A Nonpatent Literature NPLT 1. Urisu et al., Analytical and Bioanalytical Chemistry, (2008), 391:2703-2709

SUMMARY OF INVENTION

Technical Problem

In this regard, in a planar patch clamp device, a reservoir holding a pipette solution or other conductive liquid is arranged at lower side of the through holes of the substrate and supplying/discharging path is connected to the reservoir to introduce or replace this liquid. A bottom electrode is usually provided in this path. However, there were the problems that conductive liquid easily leaked through the supplying/discharging path and even at the time of non-measurement, current easily leaked through the supplying/discharging path to the lower electrode, and the electrode easily deteriorated.

Further, when applying a planar patch clamp device to various types of screening, high throughput is extremely important. In principle, high throughput is achieved by arranging a large number of single channel patch clamp devices. However, in such a configuration of patch clamp devices, the overall hardware ends up becoming larger in size and bulky, electrodes have to be arranged for each device, and maintenance and replacement work become necessary.

In particular, in the culture type planar patch clamp method, as described in the Japanese Patent Publication No. 2009-204407A (PLT 3), a substrate on which an extracellular matrix-forming substance is deposited at the rims of the through holes is used. For this reason, as disclosed in the pamphlet of the International Publication No. 2013/094418A (PLT 4), a slight gap is formed between the cell membranes of the trapped cells and the substrate surface, and thus the seal resistance falls. In addition, the leakage current flows across this gap, thereby the noise current increases in contrast with the fluctuation of the applied membrane potential. Accordingly, in order to reduce fluctuations in the applied membrane potential, precise and fine electrode parts obtained by placing AgCl/Ag wire comprised of silver wire with a chlorinated surface in containers, filling the containers with a saturated solution of KCl and AgCl dissolved in saturated states, making the ends of the electrode containers out of an inorganic porous material, and sealing in the saturated electrode solution (salt bridge type electrode parts) are used. The electrode parts require the work of disassembly and washing of electrode parts, replacement of saturated electrolyte, replacement of the electrode parts themselves, etc., after each short time of use (for example one day etc.) At the time of replacement of the saturated electrolyte in the salt bridge type electrode parts, careful attention is required to prevent the entry of air bubbles. As a result, the work and time consumed for maintenance become tremendous. With multiple as, maintenance becomes further difficult.

Solution to Problem

The inventors engaged in intensive studies in consideration of such problems and as a result devised a planar patch clamp device having configurations of arranging a valve (preferably microvalve) at the supply/discharge path between the reservoir at the opposite side to the cell arrangement surface of the substrate and an electrode part, and using the valve to allow or stop the flow of electrolyte and electrical conduction, and thereby solved the above problem.

That is, the gist of the present invention is as follows:

[1] A planar patch clamp device comprising:
an electrical insulating substrate having a first surface having a cell arrangement region and a second surface of the opposite surface and having a through hole in the cell arrangement region which do not pass cells, but pass liquid;
a first reservoir provided at the first surface side of the electrical insulating substrate to be able to communicate with the through hole and hold a first conductive liquid;
a first electrode part arranged to be able to be electrically conductive with the first reservoir through the first conductive liquid;
a second reservoir provided at the second surface side of the electrical insulating substrate to be able to communicate with the through hole and hold a second conductive liquid;
a second electrode part arranged to be able to be electrically conductive with the second reservoir through the second conductive liquid;
a supply path connected to the second reservoir and supplying the second conductive liquid to the second reservoir;
a discharge path connected to the second reservoir and discharging the second conductive liquid from the second reservoir; and
a valve provided in the supply path and/or discharge path, able to allow or stop the flow of the second conductive liquid, and also able to allow or stop electrical conduction between the second reservoir and the second electrode part.

[2] The planar patch clamp device according to [1], wherein
the electrical insulating substrate has a plurality of cell arrangement regions and corresponding through holes and is provided with a plurality of second reservoirs corresponding to the plurality of cell arrangement regions,
the supply path has a main supply path and a plurality of branch supply paths respectively branched from the main supply path and connected to the plurality of second reservoirs,
the discharge path has a plurality of branch discharge paths respectively connected to the plurality of the second reservoirs and a main discharge path where the plurality of branch discharge paths merge,
the second electrode part is provided at the main supply path and/or main discharge path, and
a valve is provided at each branch supply path and/or each branch discharge path.

[3] The planar patch clamp device according to [1] or [2], wherein an electric resistance before and after the valve is 1 megaohm or more at the time of valve closing.

[4] A planar patch clamp system comprising: the planar patch clamp device according to any one of [1] to [3];
a control part controlling opening and closing each valve of said planar patch clamp device; and
an electrical detecting part detecting an electrical signal at each electrode part of the planar patch clamp device.

[5] The planar patch clamp system according to [4] comprising a plurality of the planar patch clamp devices.

[6] The planar patch clamp system according to [4] or [5] further comprising an optical detecting part for detecting an optical signal derived from a cell arranged on the planar patch clamp device.

[7] A method for screening drugs having an effect on a nerve cell network by using the planar patch clamp device according to any one of [1] to [3] or the planar patch clamp system according to any one of [4] to [7].

Advantageous Effects of Invention

According to the planar patch clamp device of the present invention, the flow of the liquid (electorolyte etc) and electrical conduction through the supply/discharge paths connected with the reservoir at lower side of the substrate (2) can be controlled together by valves, so leakage of liquid or leakage of current through the supply/discharge paths can be reliably prevented. Due to this, it is possible to prevent deterioration of the electrodes due to leakage of current at the time of non-measurement. Further, replacement of the liquid of the reservoir below the substrate also becomes easy.

Further, in a multi-channel type patch clamp comprised of a plurality of patch clamp devices, the electrode parts can be shared, thereby maintenance work of the electrode parts can be simplified and shortened. In particular, in a culture type planar patch clamp device where the maintenance work of the electrode parts is complicated, the advantage of simplifying and shortening the maintenance work of the electrode parts is extremely great, which is greatly contributed to high throughput of the device. Furthermore, due to sharing of electrode parts, the device can also be made smaller in size.

Further, according to the composite type planar patch clamp system provided with a plurality of planar patch clamp devices of the present invention, the electrode parts can be shared among the planar patch clamp devices. Due to this, further higher throughput is achieved.

BRIEF DESCRIPTION OF DRAWINGS

FIG. 3(a) is a perspective view of a microvalve (31), FIG. 3(b) is a top view of the microvalve (31) of FIG. 3(a), and FIG. 3(c) is a cross-sectional view along a-a' and b-b' of the microvalve (31) of FIG. 3(a). In FIGS. 3(a) to 3(c), the left side figure shows a microvalve (31) in the closed state, while the right side figure shows a microvalve (31) in the opened state.

FIG. 4C is a schematic view showing one example of the configuration of a multi-channel type planar patch clamp device in the case of providing two electrode parts.

FIG. 5(*b*) is a conceptual view showing one example of the configuration of a path of the composite multi-channel type planar patch clamp device (1*b*) of FIG. 5(*a*). FIG. 5(*c*) is a schematic view showing a substrate arrangement region in which four multi-channel type planar patch clamp substrates are arranged in the composite multi-channel type planar patch clamp device (1*b*) of FIG. 5(*a*).

FIG. 8(*a*) shows an image of $Ca^{2+}$ imaging performed utilizing one channel in the 20 channels of the composite multi-channel type planar patch clamp device (1*b*) shown in FIG. 5. FIG. 8(*b*) is a graph showing a change along with the elapse of time of the fluorescence intensity obtained by $Ca^{2+}$ imaging of the active potential observed at the cells 1 to 4 shown in FIG. 8(*a*) when applying current two times in the cell 1 shown in FIG. 8(*a*).

FIG. 11B shows a channel current generated according to an applicable membrane potential in the case adding glutamic acid.

FIGS. 12(*a*) to 12(*c*) are views focusing on the applied membrane potential of FIG. 11 of −20 mV channel current and calculating and graphing the area of each pulse-like wavelength observed. The abscissas show the areas of the pulses, while the ordinates show the number of pulses of predetermined areas. The total of the channel current pulses is shown in FIG. 12(*d*).

FIGS. 13(*a*) to 13(*c*) are photos showing results of $Ca^{2+}$ imaging in a formed neural network. FIG. 13(*a*) shows the results of $Ca^{2+}$ imaging and measurement in the non-added state, FIG. 13(*b*) shows the results of $Ca^{2+}$ imaging in the state adding a buffer solution (500 μl) containing 10 μM concentration glutamic acid after this, and FIG. 13(*c*) shows the results of $Ca^{2+}$ imaging in the state adding 2.5 mM D-AP5 and 2.5 mM CNQX after adding glutamic acid.

DESCRIPTION OF EMBODIMENTS

[Summary]

The planar patch clamp device of the present invention is configured to arrange a valve (preferably microvalve) at a path between the reservoir at the side opposite to the cell arrangement surface of the substrate and an electrode part; and control to allow or stop the flow of electrolyte and electrical conduction by the valve. In the planar patch clamp device, a single pair of paths of the supply path and discharge path is provided for each single-channel device.

The inventors discovered that by providing a supply path and/or discharge path with a valve, preferably a microvalve, it is possible to share electrode parts, reduce the size of the device, and simplify and shorten maintenance work without greatly changing the overall operating time.

That is, the time required for a microvalve to open or close a micropath is usually several seconds or less. Further, when recording the channel current from an electrode, the speed of response of the electronic circuit when switching one channel to another channel is always an extremely short microsecond or so. The inventors took note of these points and created a configuration connecting a plurality of (for example, "n" number of) branch supply paths and discharge paths connected to a plurality of (for example, "n" number of) single-channel devices to a respective single main supply path and main discharge path, setting a single electrode so as to be conducive with the solution in the main supply path and/or main discharge path, and making only the branch supply path and/or branch discharge path of the single-channel device to be measured the opened state by a microvalve.

Due to such a configuration, it becomes possible to reduce the number of electrodes (to for example 1/n) without greatly changing the overall operating time. Further, microvalves are much small than electrodes, so the dimensions of the device as a whole can also be greatly reduced.

[Single-Channel Type Patch Clamp Device]

Figure 1:
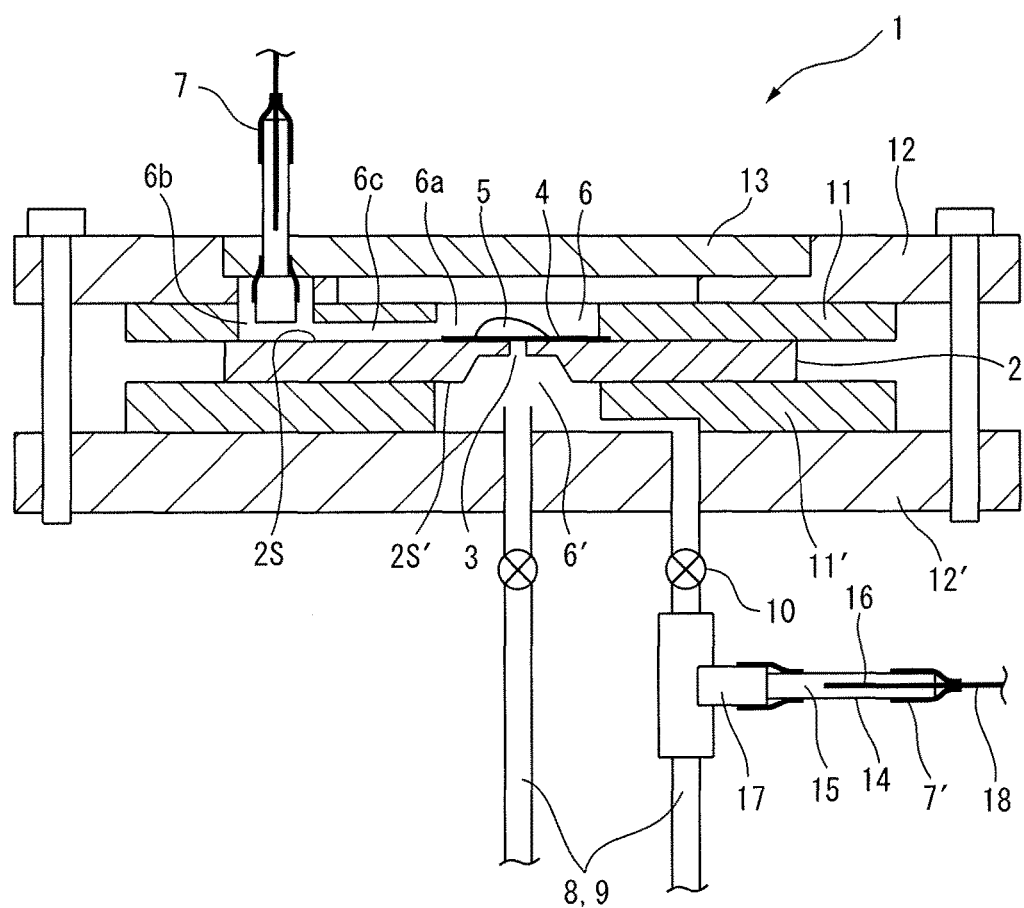
FIG. 1 is a schematic view showing one example of the configuration of a single-channel type planar patch clamp device (1).

First, a single-channel type planar patch clamp device (this being suitably abbreviated as a "single-channel device") will be explained. A single-channel device is a device having a single structural unit enabling measurement by the planar patch clamp method (this being referred to as a "channel"). FIG. 1 shows a schematic cross-sectional view of a single-channel type planar patch clamp device (single-channel device) (1) according to one embodiment of the present invention. However, the planar patch clamp device of the present invention is not limited to the single-channel device (1) of FIG. 1.

The single-channel device (1) of FIG. 1 has an electrical insulating substrate (2) having a first surface (2S) and a second surface (2S'). At the first surface (2S) of the electrical insulating substrate (2), a cell arrangement region (4) is arranged. Inside the cell arrangement region (4), a through hole (3) communicating the first surface (2S) and the second surface (2S') is provided. The size of the through hole (3) is set to a size which does not pass a cell (5) arranged at the cell arrangement region (4), but can pass a liquid. Therefore, the inside diameter of the through hole (3) may be suitably selected in accordance with the size of the cell (5) used. For example, from the viewpoint of using a nerve cell, the inside diameter of the through hole (3) is preferably 1 to 3 μm or so, but the invention is not limited to this.

The material of the electrical insulating substrate (2) is also not limited. For example, a glass, ceramic, plastic, or other substrate may be suitably selected. However, from the viewpoint of irradiating a laser from the bottom surface and observation by a microscope, a transparent substrate is preferable. Further, the electrical insulating substrate (2) may be formed from a single material or may be formed from a plurality of materials mixed or stacked together. As one example, when using a silicon substrate, a silicon substrate having a structure comprised of a silicon layer at the first surface (2S) side, an intermediate silicon oxide layer, and a silicon layer at the second surface (2S') side successively stacked (SOI (Silicon on Insulator) substrate) is preferable. In a silicon substrate of such a stacked structure, an intermediate layer with an extremely high insulating property is provided between two silicon layers, so a high resistance state can be established when closing the ion channel of a measured cell (5) and background noise can be reduced.

When using an SOI substrate, the thickness of the intermediate layer is preferably greater from the viewpoint of reducing the parasitic capacitance and increasing the insulation resistance. Further, if the intermediate layer is not sufficiently thick, sometimes the capacity will become larger, the resistance will become lower, and noise will increase. Accordingly, the thickness of the intermediate layer is for example 5 nm or more, in particular 10 nm or more, still more preferably 100 nm or more. On the other hand, if the intermediate layer is too thick, forming a hole becomes no longer easy. From these viewpoints, the thickness of the intermediate layer is preferably 10 μm or less, more preferably 1 μm or more, still more preferably 500 nm or less.

Further, at the surrounding part of through hole (3) at the surface of the substrate (2), it is preferable to coat an extracellular matrix-forming substance required for the cell (5) to survive on the solid surface and then place the cell (5) on the hole. Due to this, the cell (5) can be cultured while its channel ion current is continuously measured over a long period of time. For details of the culture type planar patch clamp method using such an extracellular matrix-forming substance, see Japanese Patent Publication No. 2009-204407A (PLT 3) by the inventors and Urisu et al., Analytical and Bioanalytical Chemistry, (2008), 391: 2703-2709 (NPLT 1). As the extracellular matrix-forming substance able to be used, polylysine, collagen (type I, type II, type IV), fibronectin, laminin, proteoglycan (versican, decorin, etc.), proteoglycan (aggrecan), link protein, entactin, tenascin, proteoglycan (chondroitin sulfate proteoglycan, heparin sulfate proteoglycan (perlecan etc.), keratin sulfate proteoglycan, dermatan sulfate proteoglycan), hyaluronic acid (one type of glycosaminoglycan), elastin, fibrin, etc. may be illustrated, but the invention is not limited to these.

Further, it is preferable to form a cell fixing location surrounded by protrusions (see reference numeral (25) of FIG. 6 explained in the later "composite multi-channel type planar patch clamp device") at the surrounding part of the through hole (3) at the surface of the substrate (2). Due to this, in particular when measuring a nerve cell, it becomes possible to restrict the movement of the nerve cell while forming a neural network. For details of the planar patch clamp method using a cell fixing location surrounded by such protrusions (25), see International Patent Publication No. PCT/JP2013/57976 (WO2014/045618) of the inventors. Specifically, a plurality of, for example, three, four, five, six, or more, protrusions (25) may be provided around a through hole (3) of the substrate surface to obstruct movement of the cell (5). Between the protrusions (25), wide intervals are set to an extent not permitting passage of the cell body of the nerve cell. The inside diameter of the cell fixing location defined by the plurality of protrusions (25) is a size enabling the cell bodies of one to nine, preferably one to five, nerve cells to be held. Instead of the protrusions (25), it is also possible to form a recess having a width and depth larger than the cell (5) and use it as a cell fixing location. Further, by connecting a plurality of these recesses together by grooves with widths smaller than the cell bodies, it becomes possible to restrict movement of nerve cells while forming a neural network.

At the first surface (2S) side of the electrical insulating substrate (2), a first reservoir (6) able to communicate with the through hole (3) is provided. The first reservoir (6) holds a first conductive liquid (for example, a buffer solution or culture medium etc. called a "bath solution") filled around the cell (5) arranged in the cell arrangement region (4). The first reservoir (6), for example, is configured comprised of a main reservoir (6a) and a branch reservoir (6b) electrically connected through the introduction passage (6c). The first reservoir (6) may be provided with a passage for introducing or discharging a conductive liquid or may be provided with an opening part able to open and close by a lid member (13).

The first conductive liquid is a liquid enabling culture of cells (5) arranged in the cell arrangement region (4) and detection of an electric signal by the patch clamp method. For example, as the first conductive liquid, it is also possible to use a cell culture medium and, after culturing the cells, use this in place of the bath solution for detecting an electrical signal by a patch clamp. Further, it is also possible to not replace the bath solution and perform the patch clamp with the cell culture medium as is. For the cell culture medium, any cell culture medium or differentiation inducing culture medium may be suitably selected in accordance with the type of the cell or differentiation stage. As examples of the cell culture medium, the Eagle medium, Dulbecco's Modified Eagle's medium (DMEM), Ham's F10 and F12 media, and other basal media plus salts, serum, antibiotics, growth factors, micronutrients, and other additives can be used. It is also possible to seed the cell arrangement region (4) with stem cells, for example, iPS cells, ES cells, or neural stem cells and furthermore cells in the middle of differentiation, culture them, cause differentiation to the desired cells, for example, nerve cells, and detect the electrical signals at the planar patch clamp device of the present invention. In this case, the stem cell culture medium, differentiation inducing culture medium, and nerve cell culture medium may be different culture media and can be used successively replaced. As the culture medium of motor neurons or glial cells, micronutrients such as retinoic acid, sonic hedgehock, cAMP, etc. may be added to the above cell culture medium. Growth factors such as insulin, transferrin, insulin growth factor (IGF), brain-derived neurotrophic factor (BDNF), and glial-cell derived neurotrophic factor (GDNF) may also be added. The bath solution may be any solution so long as a bath solution used in the patch clamp method. The first conductive liquid may also have various reagents added to it to stimulate the cells or enabling imaging of the cells.

Further, the first electrode part (7) is arranged so as to be electrically connected with the first reservoir (6) through the first conductive liquid. The first electrode part (7) is arranged in a state inserted in the first conductive liquid in the first reservoir (6) (for example, the branch reservoir (6b)). Further, the first electrode part (7) is supplied with a ground potential. Due to this, the first conductive liquid in the first reservoir (6) can be maintained so as to become the reference potential.

On the other hand, at the second surface (2S') side of the electrical insulating substrate (2), a second reservoir (6') able to communicate with the through hole (3) is provided. The second reservoir (6') holds a second conductive liquid. The second conductive liquid is a liquid enabling culture of the cell (5) and detection of an electrical signal by the patch clamp method. For example, as the second conductive liquid, it is possible to use a cell culture medium to culture the cell (5), then replace this with a pipette solution or other buffer solution for detecting an electrical signal by the patch clamp method. Further, the through hole (3) is an extremely small hole, so it is also possible to not use a cell culture medium but to use a pipette solution from the start to culture the cell (5). The cell culture medium may be the same as the cell culture medium used for the first conductive liquid or may be a culture medium of a different composition. The pipette solution may be any solution so long as a pipette solution used in the patch clamp method. The second conductive solution may also have dissolved into it chemical substances relating to opening or closing of the ion channel or other reagents used for experiments. In another aspect, for the purpose of forming a small hole in the cell membrane, a second conductive liquid containing a cell membrane hole-forming antibiotic may be introduced to the second reservoir (6'). The cell membrane hole-forming antibiotic includes a polyene-based antibiotic, such as, amphotericin B, nystatin, natamycin, etc.

The first reservoir (6) and the second reservoir (6') (these sometimes being together referred to as simply the "reservoirs") may be configured in any way so long as satisfying the demands for holding the conductive liquids and placing electrode parts (7, 7') to be able to communicate with the conductive liquids. For example, the reservoirs (6, 6') may be wells. Further, it is also possible to superpose insulating spacer members (11, 11') at the first surface (2S) side and/or the second surface (2S') side of the substrate (2) and provide cutaway parts at the spacer members (11,11') at positions corresponding to the reservoirs (6,6') to form the reservoirs (6,6'). The spacer member present at the first surface is made the first spacer member (11) while the space member present at the second surface is made the second spacer member (11'). Furthermore, by arranging a first plate member (12) at the outermost circumference of the first spacer member (11) at the side opposite to the substrate and arranging a lid member (13) at the plate member, it is also possible to make the first reservoir (6) a closed space or liquid-tight. It is also possible to further arrange a second plate member (12') at the second spacer member (11') at the side opposite to the substrate to make the second reservoir (6') liquid-tight. The second plate member (12') has a supply path (8) and discharge path (9) connected to the second reservoir (6') passing through it.

While not necessarily limited to this, the spacer members (11, 11') may be any members so long as insulating members. They may be the same material as the insulating substrate (2) or may be different. From the viewpoint of suppressing scattering of light by laser excitation, the first spacer member (11) of the first surface (2S) side is preferably comprised of a light blocking material, while from the viewpoint of observation by a microscope, the second spacer member (11') of the second surface (2S') side is preferably comprised of a light passing material.

Further, the second reservoir (6') is connected to a supply path (8) supplying the second conductive liquid to the second reservoir (6') and to a discharge path (9) discharging the second conductive liquid from the second reservoir (6'). The supply path (8) and discharge path (9) may be any materials. They may be configured by tubes made of Teflon®, polyvinyl chloride, etc., but from the viewpoint of providing the later explained valves (10), it is preferable to use micropaths etc., formed by using a mold formed with a resist pattern by photolithography etc., on the surface of a silicone substrate so as to transfer a PDMS (polydimethyl siloxane) or RTV (room temperature vulcanizing) rubber or other silicone rubber. By using such micropaths, assembly of the planar patch clamp device becomes extremely easy and problems such as offset of the paths can be avoided. The supply path (8) and discharge path (9) may be any sizes, but, for example, have a width of 100 μm and a height of about 50 μm. The supply path (8) is connected with a storage tank storing the second conductive liquid and is supplied with liquid by a pump arranged at any location of the path. The supplied second conductive liquid is discharged through the discharge path (9). The pump may be a pressurizing drive system or a suction drive system. Preferably, the pump is a liquid suction device arranged in the discharge path (9), so the second reservoir (6') can be given a negative pressure. By giving a negative pressure, it is possible to make the seal of the through hole (3) by the cell (5) present at the through hole (3) stronger. Due to this, it is possible to raise the seal resistance between the cell (5) and the electrical insulating substrate (2). On the other hand, in another aspect, it is also possible to apply a stronger negative pressure for the purpose of forming a hole in the cell membrane and possible to achieve a whole-cell mode.

Further, a second electrode part (7') is arranged so as to be electrically conductive with the second reservoir (6') through the second conductive liquid. This second electrode part (7') is usually provided at the supply path (8) or discharge path (9) so that it contacts the second conductive liquid when introducing the second conductive liquid in that path. Due to this, the invention is configured so that the potential of the second conductive liquid in the second reservoir (6') and the paths can be measured through the second electrode part (7'). Further, the invention is configured so that any voltage can be applied through the second electrode part (7') to the second conductive liquid in the second reservoir (6') and the paths.

Figure 2:
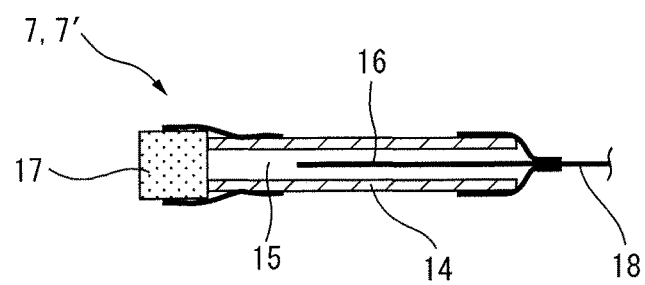
FIG. 2 is a schematic view showing one example of the configuration of salt bridge type electrode parts (7, 7').

Note that, as the first electrode part (7) and the second electrode part (7') (these sometimes being together simply referred to as the "electrode parts"), it is possible to use various known types of electrode parts used for conventional planar patch clamp devices. However, in the above-mentioned culture type planar patch clamp device, compared with a pipette patch clamp device or nonculture type planar patch clamp device, it is known that the seal resistance is extremely low and noise current easily occurs due to fluctuations in the interfacial potential of the electrodes. Accordingly, from the viewpoint of greatly preventing fluctuations in the interfacial potential of the electrodes and reducing the noise current, in the present invention, as electrode parts, it is preferable to use salt bridge type electrode parts reported by the inventors etc. in the pamphlet of International Patent Publication No. 2013/094418 (PLT 4) etc. One example of the configuration of this salt bridge type electrode part is schematically shown in FIG. 2. The salt bridge type electrode part (7,7') of FIG. 2 is configured by placing an Ag/AgCl electrode (16) comprised of silver wire with a chlorinated surface in an electrode container (14) filled with a KCl saturated solution as an electrode solution (15) and sealing the tip of the electrode container (14) contacting the pipette solution by an inorganic porous material (17). The Ag/AgCl electrode (16) is connected to a lead through an electrode pin (18). Due to this configuration, even if there are fluctuations in the salt concentration of the pipette solution, almost no fluctuation in potential is caused at the interfacial potential between the Ag/AgCl electrode (16) and electrode solution (15) contacting the same, so it is possible to keep the noise current extremely low.

Furthermore, in the single-channel device (1) of FIG. 1, the supply path (8) and/or discharge path (9) is provided with a valve (10). This valve (10) is configured to be able to allow or stop the flow of the second conductive liquid and allow or stop the electrical conduction between the second reservoir (6') and the second electrode part (7'). That is, if the valve (10) is open, flow of the second conductive liquid is allowed and electrical conduction is allowed through the second conductive liquid, while if the valve (10) is closed, the valve (10) stops the second conductive liquid and electrical conduction is cut by the resistance value around the valve (10). Here, both the supply path (8) and the discharge path (9) may have valves (10) arranged at them. In this case, these valves (10) may be controlled to open and close together or may be controlled to open and close individually. On the other hand, a valve (10) may be arranged at only one of the supply path (8) or discharge path (9). In this case, the path at which the valve (10) is arranged may be provided with the second electrode part (7').

Therefore, the valve (10) is a nonconductive or insulating valve. Specifically, the electrical resistance value at the time of closing is, for example, preferably 1 megaΩ or more, more preferably 3 megaΩ or more, still more preferably 5 megaΩ or more, further more preferably 10 megaΩ or more. The upper limit value of the electrical resistance value is not particularly limited.

The type of the valve (10) is not limited, but as an example a microvalve which can open and close a micropath may be mentioned. A microvalve is a valve which allows and stops the flow of liquid in a micropath and usually has a micropath formed by an elastic material, a movable valve arranged adjoining the micropath, and a drive system able to drive the movable valve. When opening the microvalve, the movable valve is present at a position not substantially pressing against the micropath and allows the flow of liquid in the path. When closing the microvalve, the drive system makes the movable valve displace to a position pressing against the micropath, makes the micropath deform to close the inside hole of the path, and stops the flow of liquid in the path. As the drive system, a pressure drive system using fluidic pressure, such as compressed air or a liquid, etc., as the drive source or a mechanical drive system etc. using a piezo element etc. may be mentioned. Various such microvalves are known. In the present invention, any can be used, but as one example, the liquid pressure control microvalve disclosed by Stephen Quake etc. (Journal of Applied Physics, vol. 95, (2004) 393-398) etc. may be mentioned.

Figure 3:
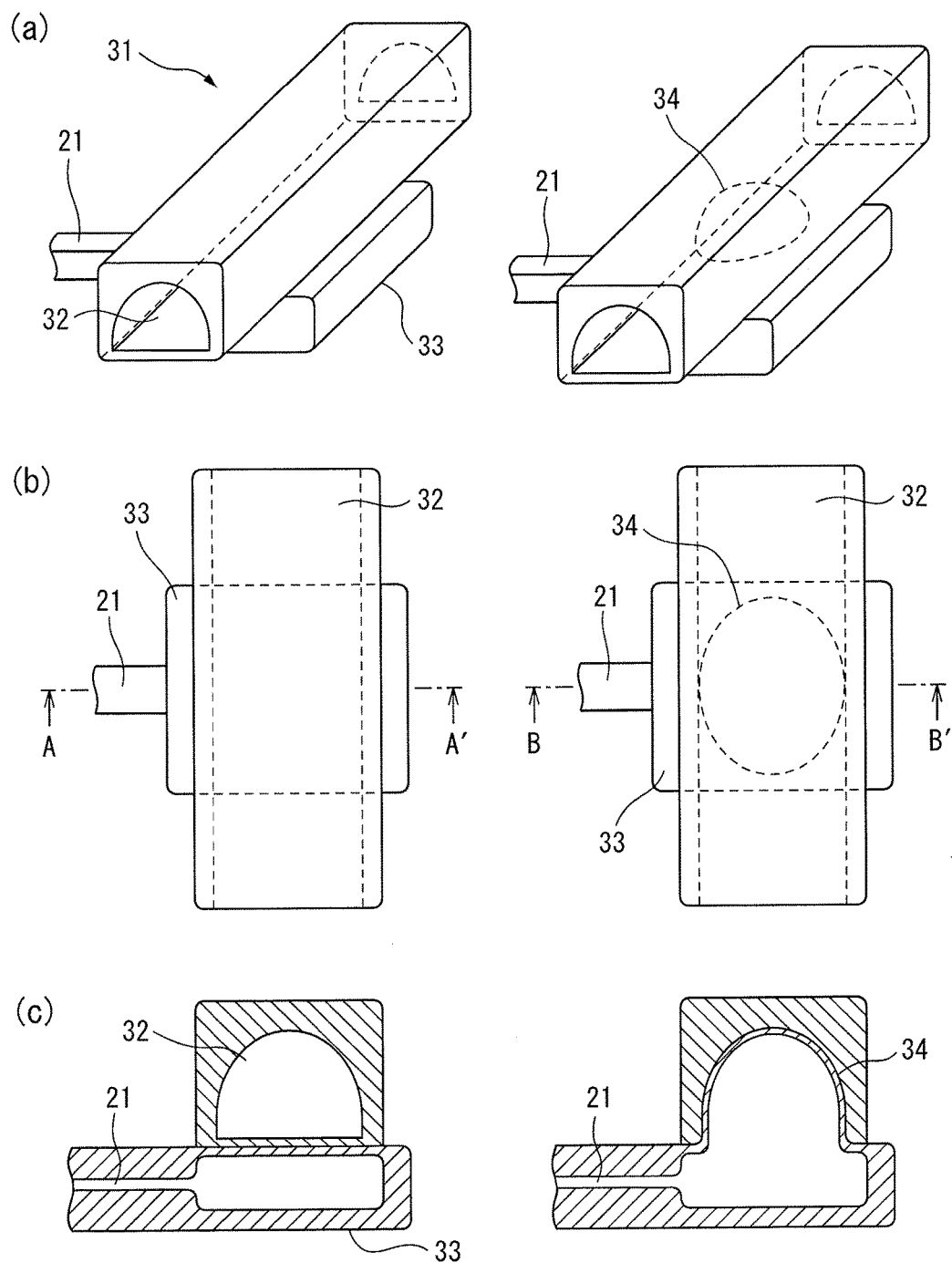
FIGS. 3(a) to 3(c) are schematic views showing examples of the configuration of a microvalve (31).

Here, one example of the configuration of a microvalve in the planar patch clamp device of the present invention will be explained with reference to FIGS. 3(*a*) to 3(*c*). However, the microvalve which can be used in the present invention is not limited to this at all. FIG. 3(*a*) is a perspective view of the microvalve (31), FIG. 3(*b*) is a top view of the microvalve (31) of FIG. 3(*a*), and FIG. 3(*c*) is a cross-sectional view along A-A' and B-B' of the microvalve (31) of FIG. 3(*a*). The microvalve (31) shown in FIGS. 3(*a*) to 3(*c*) is a compressed air drive type microvalve (31) provided with a micropath (32) comprised of a flexible material (corresponding to supply path (8) or discharge path (9)), an air pressure pat (33) (movable valve) able to expand or contract arranged below the micropath (32), and a compressed air line (21) connected to the air pressure pat (33). The compressed air line (21) introduces compressed air into the air pressure pat (33) or discharges it from the air pressure pat (33) to form an air pressure drive system which causes expansion or contraction of the air pressure pat (33) through the pressure of the compressed air. In such a microvalve (31), the micropath (32) and the air pressure pat (33) are fixed with each other. If the air pressure pat (33) expands, the top surface of the air pressure pat (33) adjoining the bottom surface of the micropath (32) displaces upward whereby the bottom surface of the micropath (32) is pressed and the inside hole of the micropath (32) is made to deform to form the deformed part (34) and close it. Due to this, in the opened state of the microvalve (31) (left side figures of FIGS. 6(*a*) to 6(*c*)), the air pressure pat (33) is in the contracted state and the inside hole of the micropath (32) is opened, so the flow of liquid at the inside is allowed. On the other hand, at the closed state of the microvalve (31) (figure at right side of FIGS. 6(*a*) to 6(*c*)), compressed air is introduced from the compressed air line (21) (air pressure drive system) to the air pressure pat (33) to make it expand and the micropath (32) is made to deform to close it and thereby stop the flow of liquid at the inside. After that, if again making the microvalve (31) the opened state (left side views of FIGS. 6(*a*) to 6(*c*)), due to the compressed air line (21) (air pressure drive system), compressed air is discharged from the air pressure pat (33) whereby it is made to contract, the deformation of the micropath (32) is reversed, and the flow of liquid at the inside is restarted. In this way, the microvalve (31) can be used for control of the flow of the liquid (second conductive liquid) in the micropath (32) (supply path (8) or discharge path (9)).

Note that, the microvalve (31) used in the present invention is configured to be able to not only allow and stop the flow of the second conductive liquid in the supply path (8) or discharge path (9) but also allow and stop electrical conduction between the second reservoir (6') and the second electrode part (7') through the second conductive liquid. To realize such a microvalve (31), it is preferable to form at least the micropath (32) of the microvalve (31) part (supply path (8) or discharge path (9)) by a material having an electrical insulating ability and excellent in flexibility. Due to this, when using the movable valve to press and deform the micropath (32), the inside hole of the micropath (32) sufficiently deforms and the cavity of the inside hole is sufficiently closed by the insulating material whereby electrical conduction can be cut. As such a material having an electrical insulating ability and excellent in flexibility, for example PDMS (polydimethyl siloxane) or RTV (room temperature vulcanizing) rubber or other silicone rubber may be mentioned.

Furthermore, when using a microvalve (31) to cut electrical conduction of a micropath (32), compared with the case of stopping the flow of liquid, it is necessary to use the moving valve to strongly press the micropath (32) and more reliably seal the inside hole. The amount of displacement of the movable valve or pressure etc. required for this cannot be prescribed overall since they differ according to the configuration of the microvalve (31), but considering the configuration of the microvalve (31), a person skilled in the art could easily set them so that a sufficient electrical resistance value (for example, preferably 1 megaΩ or more, more preferably 3 megaΩ or more, still more preferably 5 megaΩ or more, further more preferably 10 megaΩ or more) is obtained.

The measurement of the ion channel current of a cell using the single-channel device (1) of FIG. 1 having such a configuration is performed by the following procedure.

First, at the cell arrangement region (4) of the first surface (2S) of the electrical insulating substrate (2), a cell (5) to be measured is placed so as to cover the through hole (3). Further, the first reservoir (6) is made a state filled with the first conductive liquid (for example the bath solution etc.), while the second reservoir (6') is made a state filled with the second conductive liquid (for example the pipette solution etc.)

Next, a fine hole is formed in the cell membrane contacting the through hole (3) to electrically connect the inside of the cell (5) and the second conductive liquid (pipette solution etc.) of the second reservoir (6') (normally called the "whole-cell" state). The method for making the cell (5) a whole-cell state is not limited, but for example the method may be mentioned of dissolving a specific antibiotic (for example nystatin or amphotericin etc.) in the second conductive liquid, introducing such an antibiotic solution to the second reservoir (6') right before measurement of the current, and bringing it into contact with the cell membrane to form a fine hole in the cell membrane (in this case, after realization of the whole-cell state and before measurement of current, the solution inside the second reservoir (6') is again replaced with second conductive liquid not containing an antibiotic).

After that, a predetermined voltage (called "membrane potential") is applied between the first electrode part and the second electrode part. Due to this, the current passing through the ion channel of the cell member can be recorded as the channel current.

Note that, in the above explained single-channel device (1), the first reservoir (6) is usually arranged at the top side of the insulating substrate (2), but the upper wall may also be configured to be able to open or close. From here, a cell is arranged at the cell arrangement region (4), a cell is taken from the cell arrangement region (4), the first conductive liquid is filled or replaced, and various other processing is performed (for example, addition of a drug solution for investigating blockers of ion channels and drug reactions of cells etc.) However, in the same way as the second reservoir (6'), the first reservoir (6) may also be provided with a supply path (8) and discharge path (9) and these may be used to fill or replace etc. the first conductive liquid.

On the other hand, the second reservoir (6') is filled or replaced with the second conductive liquid through the supply path (8) and discharge path (9). That is, the second conductive liquid is supplied from an outside supply source (not shown) through the supply path (8) and filled inside the second reservoir (6'). The liquid is usually driven by providing the supply path (8) or discharge path (9) with a pump or other drive part (not shown). Further, when there is a liquid in advance in the second reservoir (6'), it is discharged to the outside through the discharge path (9). Due to this, the liquid in the second reservoir (6') is replaced.

Here, in the single-channel device (1) of FIG. 1, the valve (10) provided at the supply path (8) and/or discharge path (9) is operated for controlling the flow or stopping of the second conductive liquid and controlling the formation and cutting of electrical conduction between the second reservoir (6') and the second electrode part. Due to this, it becomes possible to reliably prevent leakage of liquid or leakage of current through the supply path (8) and/or discharge path (9). In turn, it is possible to prevent deterioration of the electrode due to leakage of current at the time of nonmeasurement. Further, replacement of the second conductive liquid in the second reservoir (6') also becomes easy.

In the case of a culture type patch clamp device, after the cell (5) is placed, the device may be inserted into an incubator etc. to culture the cell. In this case, if considering the handling ability when placing the device in the incubator etc. or size restrictions etc., the invention may also be configured enabling the part of the device including the substrate (for example the part not containing power source or liquid source etc.) to be separated. Due to this, it becomes possible to separate only part of the device and place it into the incubator. In particular, by arranging the valve (10) at the end of the separated part, at the time of separation, the valve (10) can be set off and the flow of liquid from the path can be prevented. At the time of measurement of the current, the first reservoir (6) is made a state filled with the first conductive liquid (for example, the bath solution etc.), while the second reservoir (6') is made a state filled with the second conductive liquid (for example, the pipette solution etc.)

[Multi-Channel Type Planar Patch Clamp Device]

Figure 4A:
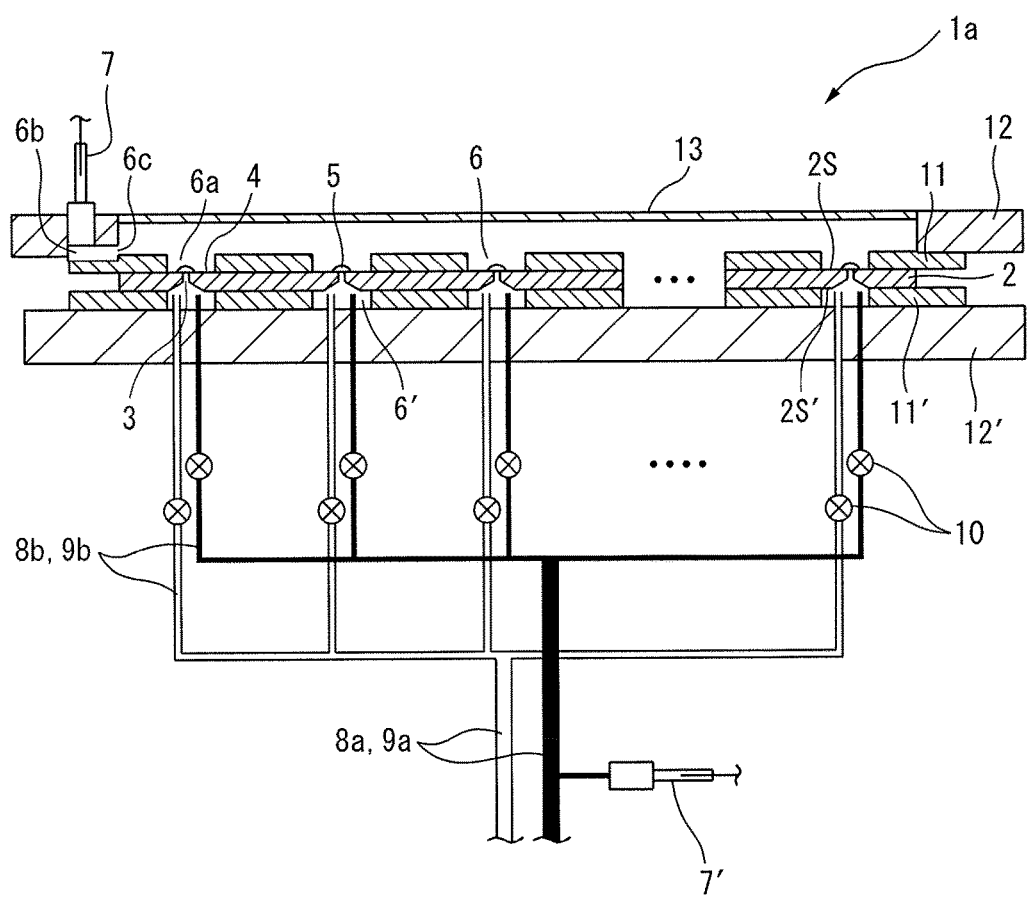
FIGS. 4A and 4B are schematic views showing one example of the configuration of a multi-channel type planar patch clamp device (1a).
Figure 4B:
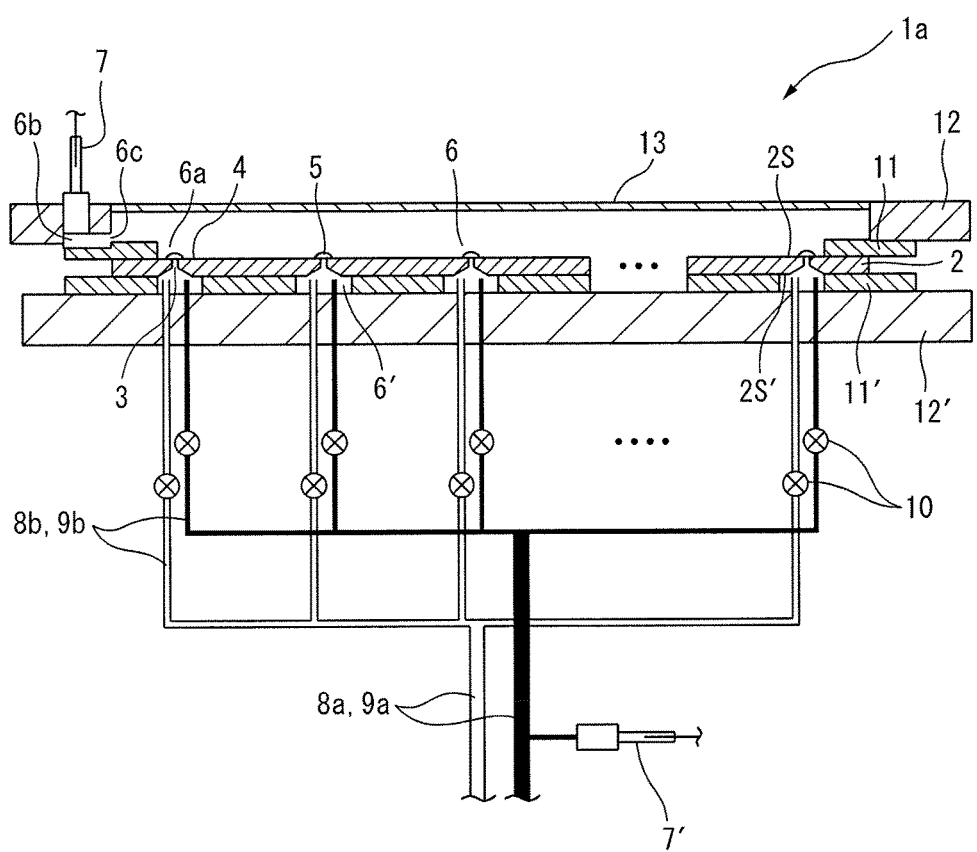

Next, a multi-channel type planar patch clamp device combining a plurality of single-channel devices (this being suitably abbreviated as a "multi-channel device") will be explained. The multi-channel type planar patch clamp device is a device having a plurality of structural units (channels) enabling measurement by the planar patch clamp method. FIG. 4A is a schematic cross-sectional view of a multi-channel type device (1a) according to one embodiment of the present invention. However, the planar patch clamp device of the present invention is not limited to the multi-channel device (1a) of FIG. 4A. For example, as shown in FIG. 4B, in the first reservoir (6), the cell arrangement regions can be consecutive, so that a neural network can be formed by the cells being measured. Furthermore, as shown in FIG. 4C, it is also possible to provide two or more supply/discharge systems provided with second electrode parts. The valves of the supply/discharge paths may be used to select the cells to be measured by the respective supply/discharge systems. Due to this, it is possible to measure the changes in current or changes in potential at the cells forming the cell network at two or more measurement points and possible to use the valves to switch cells to be measured.

In the multi-channel type device (1a) of FIGS. 4A to 4C, the electrical insulating substrate (2) has a plurality of cell arrangement regions (4) and through holes (3) corresponding to the same. Further, a plurality of second reservoirs (6') are also provided corresponding to the plurality of cell arrangement regions (4).

Further, the supply path (8) is comprised of a main supply path (8a) and a plurality of branch supply paths (8b) branched from the main supply path (8a). The plurality of branch supply paths (8b) are respectively connected to the plurality of the second reservoirs (6').

Further, the discharge path (9) is also comprised of a main discharge path (9a) and a plurality of branch discharge paths (9b) branched from the main discharge path (9a), while the plurality of branch discharge paths (9b) are connected to the plurality of second reservoirs (6').

Further, a second electrode part (7') is provided at the main supply path (8a) and/or main discharge path (9a). Further, the branch supply paths (8b) and/or branch discharge paths (9b) connected to the plurality of the second reservoirs (6') are provided with valves (10). In paths in which the second electrodes are not arranged, the branch paths need not merge to form main paths. For example, when a second electrode part (7') is arranged at the main supply path (8a), the branch discharge path (8b) need not form a main discharge path and may discharge as it is. The rest of the configuration etc. is similar to the multi-channel type device (1) of FIG. 1.

The ion channel current of a cell (5) is measured using the multi-channel type device (1a) of FIGS. 4A to 4C having this configuration by the following procedure.

First, at each of the plurality of cell arrangement regions (4) of the first surface (2S) of the electrical insulating substrate (2), a cell (5) to be measured is arranged so as to cover the through hole (3). Further, the first reservoir (6) is made a state filled with the first conductive liquid (for example, the bath solution etc.), while the second reservoir (6') is made a state filled with the second conductive liquid (for example, the pipette solution etc.)

Next, a fine hole is made in the surface of the cell membrane contacting the through hole (3) to obtain a state where the inside of the cell and the second conductive liquid (pipette solution etc.) of the second reservoir (6') are electrically conducted (whole-cell state).

Next, the valve (10) of the supply path (8) and/or discharge path (9) of the channel desired to be measured is opened and all of the other valves (10) are closed thereby only the cell (5) on the channel desired to be measured is connected through the second conductive liquid to the second electrode part (7').

After that, a predetermined voltage (called "membrane potential") is applied between the first electrode part (7) and the second electrode part (7'). Due to this, it is possible to record the ion channel current of the cell (5) present in a desired channel.

Note that, in the multi-channel type device of FIGS. 4A to 4C, there are a plurality of cell arrangement regions (4) at the first reservoir (6) and there are a number of through holes (3) corresponding to the cell arrangement regions (4). Here, it is also possible to add partitions between the cell arrangement regions (4) and thereby divide the first reservoir (6) into a plurality of reservoir sections (22). The partitions may be formed by partition members (23). For example, when superposing the first spacer member (11) at the first surface (2S) side of the substrate (2), it is possible to place the partition members (23) at the cutaway parts of the first spacer member (11) to thereby form the reservoir sections (22). When there are a plurality of reservoir sections (22), first electrode parts (7) may be set in the respective reservoir sections (22). However, by allowing electrical conduction between these plurality of reservoir sections (22), a single first electrode part (7) can be used to measure the electrical signals for all of the cells (5) of the cell arrangement regions (4) of the reservoir sections (22). Therefore, in this case, as the partition members (23), electrically conductive members, for example, metal or porous materials may be used. By using insulating members and further preventing almost all movement of liquid by using sufficiently narrow passages for connection, electrical conduction can be achieved between reservoir sections (22). By dividing the first reservoir (6) into a plurality of reservoir sections (22), the effects of drugs added to the reservoir sections on cells, the responses of the ion channels, etc. can be measured by selecting a channel to be measured by opening and closing the microvalves (31), that is, the measured reservoir section (22) of the first reservoir (6), and therefore it becomes possible to measure the effects of a plurality of drugs in a short time and becomes possible to use the device for high throughput screening. Further, the partition members (23) arranged on the substrate (2) can protect the cell fixing locations (24) comprised of the plurality of columnar protrusions (25) formed in the cell arrangement region (4) of the substrate (2) from pressure from above from a lid member (13), for example cover glass etc.

[Composite Multi-Channel Type Planar Patch Clamp Device]

Figure 5:
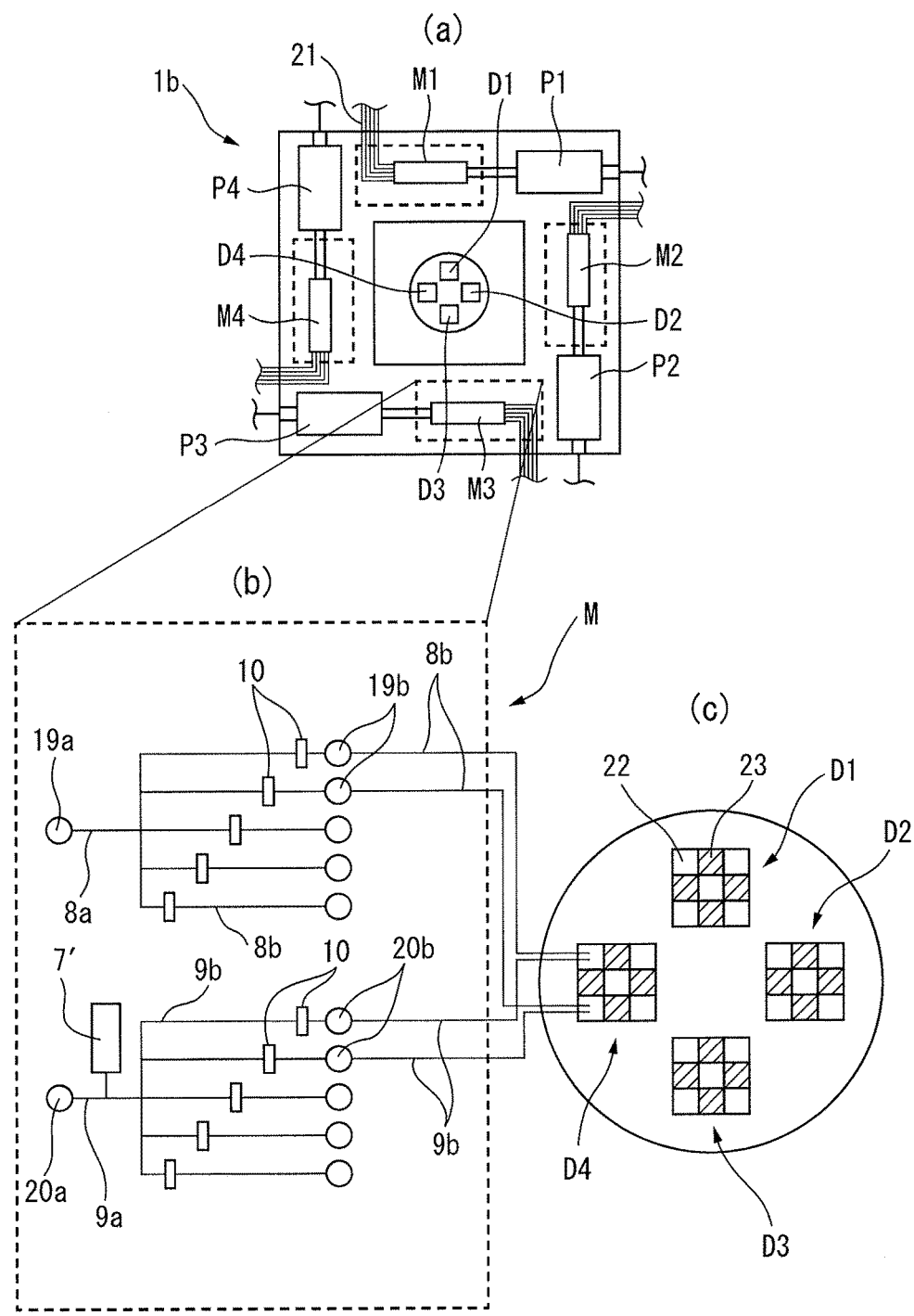
FIG. 5(*a*) is a schematic view showing one example of the configuration of a composite multi-channel type planar patch clamp device (1*b*) provided with a plurality of multi-channel type planar patch clamp devices (1*a*).

By combining a plurality of multi-channel type planar patch clamp devices, a composite multi-channel type planar patch clamp device can be configured. FIG. 5 shows one example of such a composite multi-channel type planar patch clamp device (1b), specifically shows a total 20 channel composite multi-channel type planar patch clamp device (1b) combining four 5-channel culture type planar patch clamp devices. FIG. 5(a) is a top view of this device (1b). At the center circular part, four square-type multi-channel substrates (D1 to D4) are arranged. It is possible to measure the electrical signals at the five reservoir sections (22) at these multi-channel substrates (D1 to D4). Furthermore, around the circular part, four branch path plates (M1 to M4) and four pre-amplifiers (P1 to P4) are arranged. To each branch path plate, five compressed air lines (21) able to control valves (10) are connected. Each pre-amplifier is connected on the one hand to a second electrode part (7') arranged in the branch path plate (M1 to M4) and is connected on the other hand to a device for measuring the channel current. FIG. 5(b) is an enlarged view of a branch path plate (M1 to M4). A supply system comprised of a main supply path (8a) extending from the main supply path terminal (19a) and further a branch supply path (8b) branched from the main supply path (8a), a discharge system comprised of a main discharge path (9a) extending from the main discharge path terminal (20a) and further a branch discharge path (9b) branching from the main discharge path, valves (10) allowing or stopping the flow of liquid and electrical conduction of these, and further the second electrode parts (7') are arranged. In FIG. 5(b), the compressed air lines (21) connected to the valves (10) are not shown. Only two pairs of branch supply paths (8b) and branch discharge paths (9b) are shown. The other three sets of branch supply paths (8b) and branch discharge paths (9b) are omitted so as not to complicate the illustration. FIG. 5(c) is an enlarged view of a circular part at the center of FIG. 5(a). The branch supply paths (8b) and the branch discharge paths (9b) of FIG. 5(b) are connected to one reservoir section (22) on the substrate through the branch supply path terminals (19b) and branch discharge path terminals (20b). A single second electrode part (7') is provided for the branch path plates (M1 to M4). Among the five pairs of valves (10), a predetermined single pair of valves (10) are opened and the electrical characteristics of the cell (5) present at a predetermined reservoir section (22) on the substrate can be simultaneously measured for a maximum of four channels.

Figure 6:
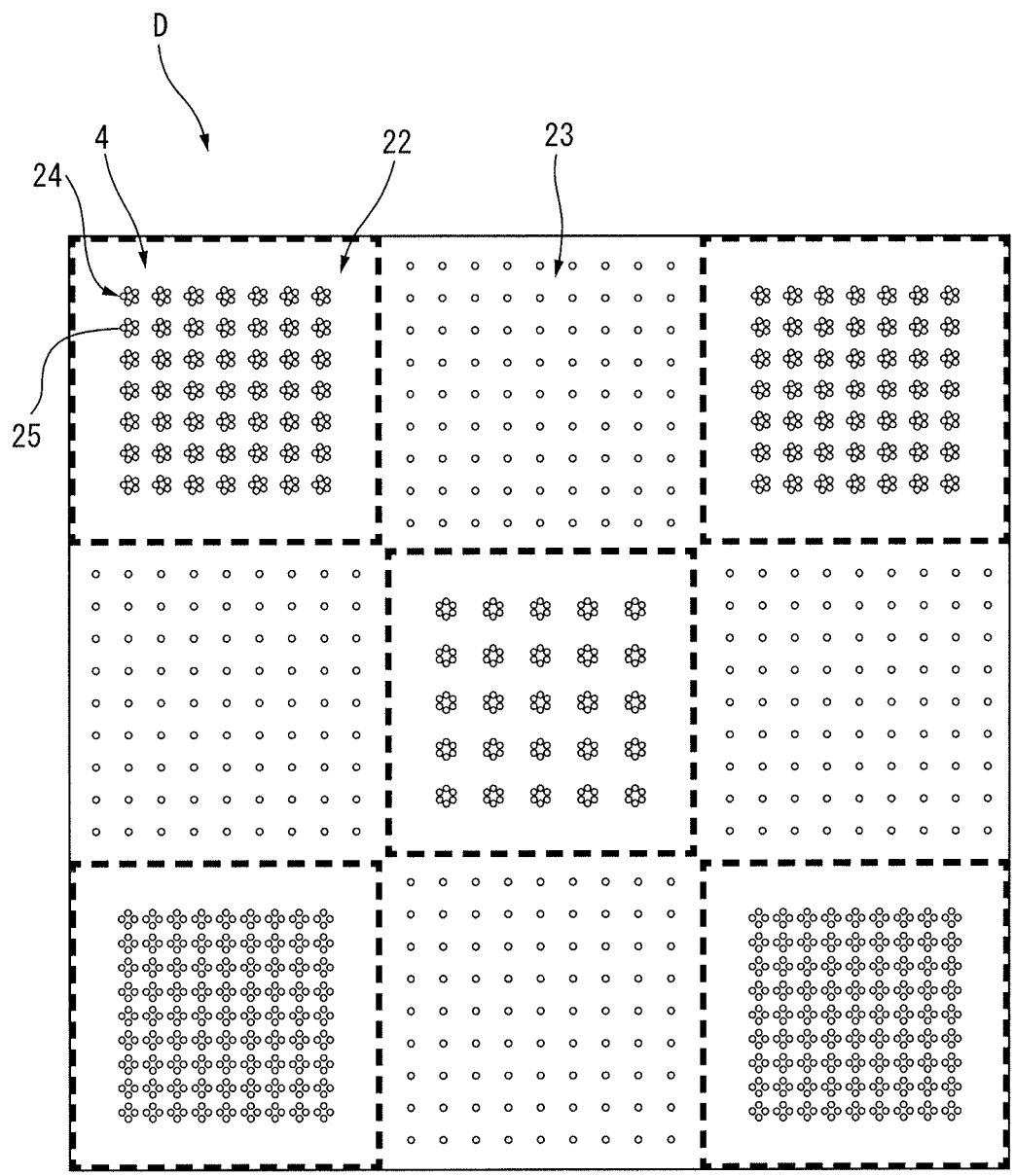
FIG. 6 is a schematic view showing one example of a multi-channel (5-channel) type planar patch clamp substrate.

FIG. 6 is a top view showing one example of a five-channel substrate (D) used as the multi-channel substrates (D1 to D4) in the composite multi-channel culture type planar patch clamp device (1b) shown in FIG. 5. This substrate is comprised of PMMA (polymethyl methacrylate) and has a thickness 200 µm square shape with 60 mm sides. This substrate has five cell arrangement regions (4) of square shapes of 20 mm sides. At the other regions, there are spacers which restrict movement of liquid. At the center part of the cell arrangement regions (4), there are diameter 1.5 to 2 µm through holes (3). At the bottom parts of the through holes (3), diameter 150 µm second reservoirs (6') are formed. The thickness of the substrate at this part is 15 µm. Each cell arrangement region (4) is formed with a large number of cell fixing locations (24). Each cell fixing location is surrounded by diameter 30 µm, height about 10 µm columnar protrusions (25). To keep a cell (5) from leaving such a cell fixing location (24), the distance between one column (25) and another column (25) is limited to 10 microns or less. By fabricating cell fixing locations (24) other than at the cell fixing locations (24) arranged at the positions of the through holes (3), it is possible to use this substrate for forming a neuron network. A second reservoir (6') under the through holes (3) is formed with a pair of a supply path (8) and discharge path (9) as micropaths.

Planar Patch Clamp System

Figure 7:
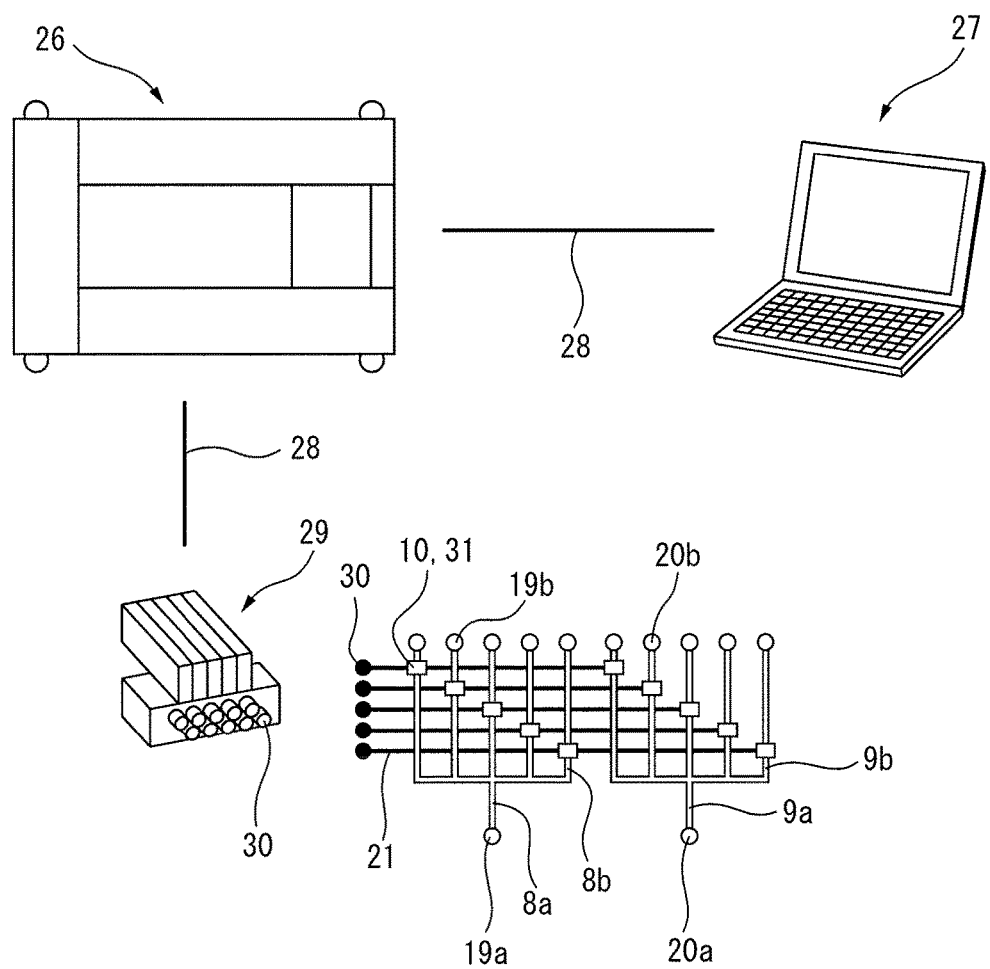
FIG. 7 is a conceptual view showing one example of the configuration of a control system of valves (10) of a multi-channel type planar patch clamp device.

The patch clamp device of the present invention is controlled by connection to the path control system and channel current measurement system. FIG. 7 is a conceptual view showing one example of the configuration of a control system of valves of a multi-channel type planar patch clamp device. The path control system uses a pump arranged in the path to generate a flow of the second conductive liquid and further operates the sequencer (26) to output control signals for operation of the valves (10) to make the valves (10) open and close and thereby allow or stop the flow of the second conductive liquid and electrical conduction. When operations of the valves (10) are controlled by compressed air, solenoid valves (29) converting the control signals output by the sequencer (26) to pneumatic pressure for controlling the valves (10) are used. The sequencer (26) and the solenoid valves (29) are connected through the connection line (28). The electrical signals transmitted to the solenoid valves (29) are converted to air pressure. Pressurized air is transmitted to the valves (10) through the compressed air line (21) connected to the solenoid valve connection terminal (30) and opens and closes the paths. The sequencer (26) is connected to the control PC (27) for path control through the connection line (28) and can be operated by a control PC (27). The channel current measurement system can use a normal system of a planar patch clamp and for example includes a current amplifier, low pass filter, and an analog-digital converter controlled by a PC for current measurement use. A PC for path control use (27) and a PC for current measurement use may operate cooperating with each other or a single PC may be used for control.

Screening Method

The planar patch clamp device, multi-channel type planar patch clamp device, composite multi-channel type planar patch clamp device, and planar patch clamp system of the present invention can be used for high throughput screening of candidate drugs having an effect on a neuron network. As the condition for screening candidate drugs, it is necessary that the channel current measured by the device of the present invention can express (1) a healthy state and (2) a diseased state and that the device be of a structure enabling proof of (3) the candidate drug being made to act on a diseased state to return to a healthy state. As shown in the examples, the planar patch clamp device of the present invention can measure the states of the above (1), (2), and (3) and can screen drugs. As the hardware configuration, it is possible to prepare a large number of single-channel devices such as shown in FIG. 1, but maintenance of the electrode parts would be difficult, so it is preferable to use a multi-channel type device such as shown in FIGS. 4A to 4C. Furthermore, as shown in the device of FIG. 5, by using a composite multi-channel type planar patch clamp device including a plurality of multi-channel type substrates (Dl to D4) and controlling the valves to successively measure the channel currents of the different reservoir sections, efficient screening becomes possible.

In the present invention, the screening method requires the step of seeding cells in the planar patch clamp device of the present invention, preferably a multi-channel type planar patch clamp device or composite multi-channel type planar patch clamp device, and forming a neuron network. After forming a neural network, it is possible to measure the channel current of a nerve cell, add a candidate drug to the first reservoir, then further measure the channel current and select a candidate drug based on the change of the channel current. In a preferable mode, it is possible to select a candidate drug which changes a wavelength of a diseased type channel current to a wavelength of a healthy type channel current as a drug effective for treatment. As the cells used, it is possible to use nerve cells acquired from humans or animals. It is also possible to seed stem cells, for example, iPS cells and ES cells, and induce differentiation to form a neural network. As the nerve cells for forming a neuron network, it is possible to use nerve cells of disease models.

The nerve cells of disease models used may be commercially available ones or may be induced by adding disease inducing agents. From the viewpoint of screening drugs, it is preferable to use nerve cells of ALS, Alzheimer's disease, Parkinson's disease, and other disease models. It is also possible to include a step of seeding healthy nerve cells, further adding a disease inducing drug to create a diseased state, and measuring the channel current in the diseased state neural network. In this case, by screening drugs causing the channel current to change from a diseased state to the normal state, it is possible to select a drug having an effect against that disease.

Above, the present invention has been explained based on specific embodiments, but the present invention is not limited to the above embodiments and can be worked modified in any way.

EXAMPLES

Below, the present invention will be further explained with reference to examples, but the present invention is not limited to the following examples and can be worked modified in any way.

Example 1

$Ca^{2+}$ Imaging of Nerve Cell Using Composite Multi-Channel Type Planar Patch Clamp Device (1b)

A composite multi-channel type planar patch clamp device (1b) of the configuration shown in FIG. 5 was prepared. Among the 20 channels of this device, the 19 pair of microvalves (31) corresponding to the 19 channels not observed were made closed states by air pressure, the single valve corresponding to the channel observed was made an open state, and voltage was applied to the second electrode part (7') and current injected so as to perform $Ca^{2+}$ imaging. More specifically, in this example, in advance, a substrate was set in a 35 mm dish filled with a nerve cell-use medium, the cell arrangement region (4) was seeded with rat cerebral cortex nerve cells, and cells were fixed at the cell fixing locations. Next, to this medium, $Ca^{2+}$ imaging-use fluorescent dye, Oregon Green BAPTA1 (invitrogen), was dissolved to a 400 nM concentration. This was allowed to stand for about 1 hour in a culture container under a 37° C., 5% $CO_2$ environment, then only the substrate was taken out from the dish and the through hole (3) was set positioned with the channel to be observed. Further, first, the first reservoir (6) was filled with a bath solution constituted by a solution of 2.5 mM $CaCl_2$, 1.25 mM $MgCl_2$, 10 mM d-glucose, 140 mM NaCl, 3 mM KCl, and 10 mM 4-(2-hydroxyethyl)-1-piperazine ethane sulfonic acid (HEPES) (pH7.4). Next, the second reservoir (6') was filled with a solution the same as the bath solution by a supply path (8) in a state applying an approximately 10 kPa negative pressure through the discharge path (9). Next, a peak value 10 μA 100 μs current was applied from the second electrode part (7') for electrical stimulus. The fluorescence generated in accordance with the concentration of $Ca^{2+}$ in the cell rising along with the electrical stimulus was observed and photographed by a fluorescent microscope equipped with a CCD camera (Nikon upright microscope Nikon LV100). The obtained fluorescence observed image is shown in FIG. 8(a). The cells were numbered 1, 2, 3, and 4. The cell 1 is present over the micro through hole (3). Current is applied to the cell 1 two times. In accordance with this, $Ca^{2+}$ flows into the cell corresponding to the generation of the active potential of the cells 1 to 4 and generation of fluorescence is observed. A graph of the change along with time of the obtained fluorescence intensity is shown in FIG. 8(b). It was observed that the active potential generated in the cell 1 is propagated to the surrounding cells 2 to 4 as well.

Example 2

Recording of Channel Current in Channel Rhodopsin Expressing Cell Using Composite Multi-Channel Type Planar Patch Clamp Device (1b)

Figure 9:
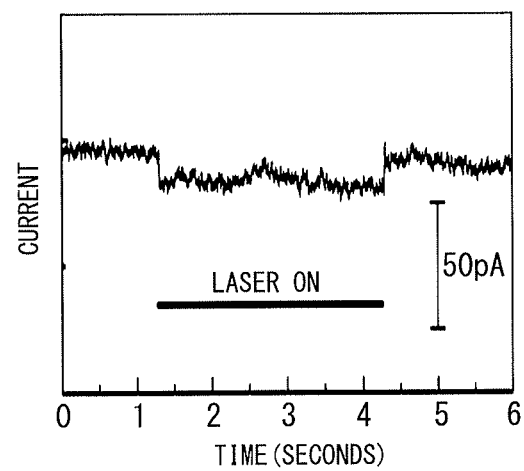
FIG. 9 is graph showing the change along with the elapse of time of the channel current in a channel rhodopsin expressing cell using a composite multi-channel type planar patch clamp device (1*b*) shown in FIG. 5.

The 19 pairs of valves corresponding to the 19 channels not observed among the 20 channels of the composite multi-channel type planar patch clamp device (1b) shown in FIG. 5 were made a closed state by air pressure and the single pair of valves of the channel being observed were made the opened state to record the channel current of the channel rhodopsin expressing cell. More specifically, the cell arrangement region (4) of the planar patch clamp device was sown with channel rhodopsin expressing HEK293 cells obtained by introducing genes of channel rhodopsin ChRWR plasmid and the cells were fixed at the cell fixing locations. For the first conductive liquid and the second conductive liquid, as the cell culture medium, a basal medium DMEM (Gibco) plus 10% FBS (Gibco), 1% GlutaMAX (Gibco), 0.5% Penicillin-Streptomycin, and 500 µg/ml G418 was used. This was cultured in a 37° C., 5% $CO_2$ atmosphere in an incubator for 5 days. Further, the planar patch clamp device was taken out from the incubator and set on the stage of the fluorescent microscope (Nikon Eclipse 80i), then a pipette was used to replace the bath solution with the first conductive liquid. Next, a −10 kPa negative pressure was applied from the discharge path (9), and a pipette solution was introduced as the second conductive liquid from the supply path (8). Next, similarly, under application of a −10 kPa negative pressure, a nystatin-containing (100 µg/ml) pipette solution was introduced from the supply path (8). Due to this, nystatin was embedded in the cell membrane of the through hole (3) part, and the inside of the cell and the bottom reservoir were made electrically conductive in state to realize a so-called whole-cell state. Next, wavelength 473 nm laser light (power 1.5 mW) (Sumitomo Osaka Cement, LD473-F5) was fired, the channel current output obtained by the whole-cell mode was amplified by the pre-amplifier P, then was passed through a 2 kHz low pass filter, then converted by an A-D converter and the signal recorded. A graph of the changes of the obtained current along with time is shown in FIG. 9. The bath solution used is the same as Example 1. As the pipette solution, a solution of 100 mM l-glutamine, 120 mM CsOH, 50 mM HEPES, 2.5 mM $MgCl_2$, and 1.25 mM $Na_2EGTA$ (pH7.4) was used.

Example 3

Figure 10:
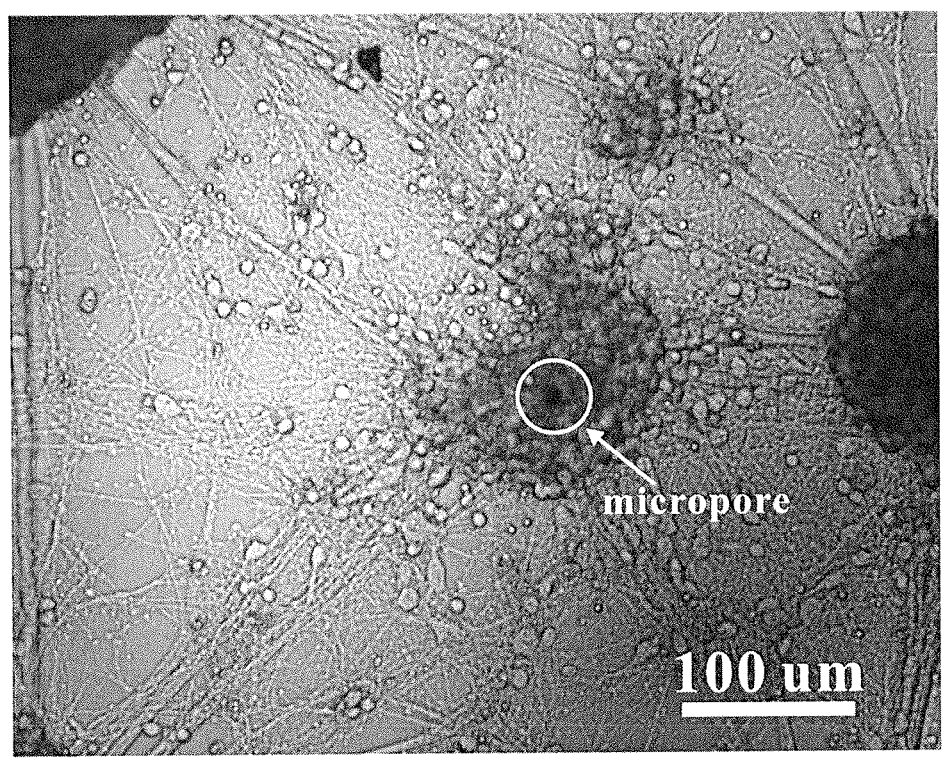
FIG. 10 is a photograph taken by an optical microscope of arrangement of nerve cells at cell fixing locations and formation of a neural network.
Figure 11A:
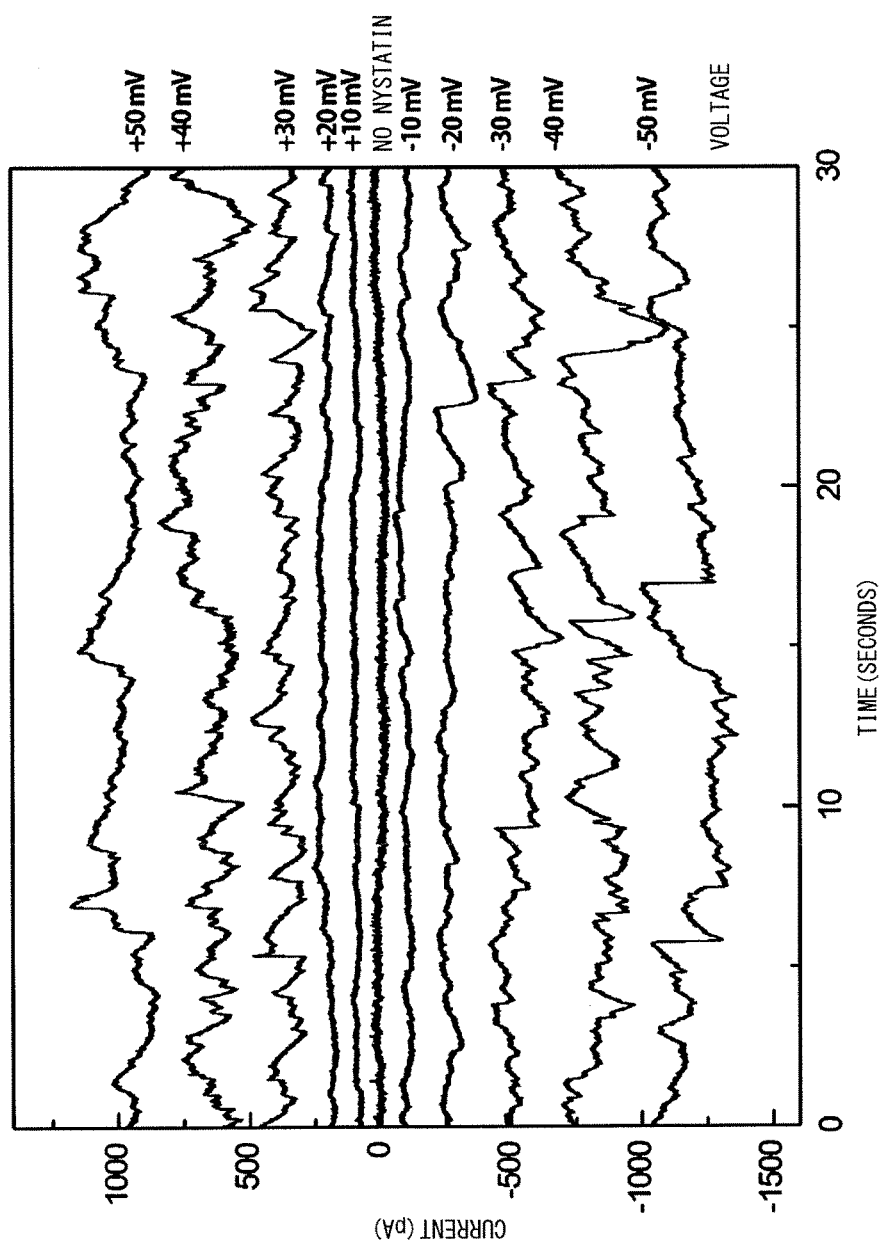
FIG. 11A shows the channel current generated in accordance with the applied membrane potential when forming small holes in nerve cells placed in the through holes to form the whole-cell mode. NoNT-n30 shows the channel current when not adding nystatin and not in the whole-cell mode. In this case, it is shown that almost no change occurs in the current.
Figure 11C:
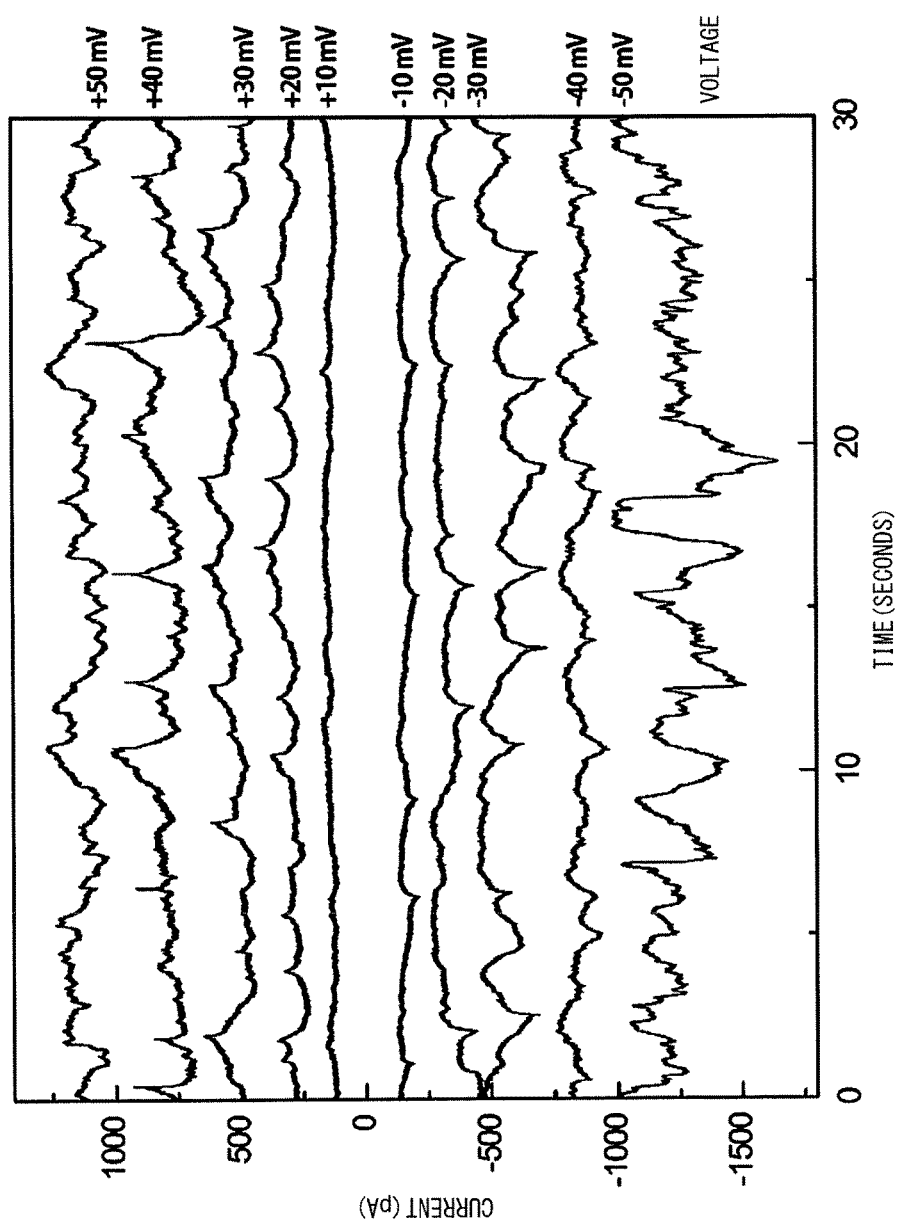
FIG. 11C shows a channel current in the case of adding an AMPA receptor antagonist and NMDA receptor antagonist after adding glutamic acid.

Screening Method Using Composite Multi-Channel Type Planar Patch Clamp Device (1b) Measurement of Change in Channel Current Administered to Drug The composite multi-channel type planar patch clamp device (1b) of the present invention was used to conduct experiments showing that high throughput screening of drugs acting on a neural network is possible. At the cell fixing locations (24) of the Si substrate surface (2S) having approximately 2 micron size through holes (3) of the composite multi-channel type planar patch clamp device (1b) shown in FIG. 5, nerve cells (5) obtained by dissecting the cerebral cortex of a rat on day 17 of birth were seeded. The commercially available nerve cell medium (Sumitomo Bakelite) was added and the result cultured in a dish for 11 days to form a neuron network which was then observed by an optical microscope (FIG. 10). Next, the Si substrate (2) on which the nerve cells (5) were placed was set on the composite multi-channel type planar patch clamp device (1b) and the reservoir sections (22) of the first reservoir (6) were filled with the bath solution (145 mM NaCl+3 mM KCl+10 mM HEPES+2 mM $CaCl_2$+8 mM Glucose+1 mM $MgCl_2.6H_2O$, pH7.3). Next, the valves set at the branch supply path and branch discharge path were made the opened state to introduce the pipette solution (140 mM KCl+10 mM HEPES+2 mM $CaCl_2$+5 mM EGTA+2 mM Mg-ATP, pH7.3) from the branch supply paths to the second reservoir. Next, the 19 pairs of valves corresponding to the 19 channels not observed among the 20 channels were made the closed state and the single pair of valves corresponding to the channel being observed were made the opened state to apply 30 mV voltage between the first electrode part (7) and the second electrode part (7') and measure the current. Before forming the whole-cell mode, the channel current was not observed. A flat baseline was recorded without regard to the applied membrane potential. Next, to the second reservoir, a nystatin solution (100 µg/ml) was introduced and a small hole was made in the cell membrane contacting the through hole to form the whole-cell mode. If forming the whole-cell mode, a channel current oscillating dependent on the applied membrane potential was observed (FIG. 11A). The applied membrane potential was made +10 mV, +20 mV, +30 mV, +40 mV, +50 mV, −10 mV, −20 mV, −30 mV, −40 mV, and −50 mV. In this state, glutamic acid was added to the first reservoir to give a final concentration of 20 µM. Due to this, changes were seen in the channel current (FIG. 11B). After measurement for about 60 minutes, to one reservoir section (22) of the first reservoir, a bath solution comprising the AMPA receptor antagonist 6-cyano-7-nitroquinoxaline-2,3-dione (CNQX)(200 µM) and NMDA receptor antagonist D-(−)-2-amino-5-phosphonopentanoic acid (D-AP5) (200 µM) dissolved in it was introduced and the channel current was again measured (FIG. 11C). Clear differences are seen among FIG. 11A, FIG. 11B, and FIG. 11C. They respectively correspond to the healthy state, diseased state due to glutamine toxicity, and state eased in glutamine toxicity by drugs. To show these states clearer, the channel current of the applied membrane potential −20 mV was focused on and the area of each pulse-like wavelength observed was calculated. The results are shown as graphs in FIG. 12(a), FIG. 12(b), and FIG. 12(c). The abscissas show the areas of the pulses, while the ordinates show the numbers of the predetermined areas. In the state of glutamic acid toxicity, the large area pulse channel current increases (FIG. 12(b)). This increase is substantially eliminated by the addition of the AMPA receptor antagonist CNQX and NMDA receptor antagonist D-AP5. The total number of the channel current pulses is shown in FIG. 12(d). The healthy state, state of glutamine toxicity, and state of elimination or easing of toxicity due to the addition of an antagonist could be observed more clearly. By filling the other reservoir sections (22) with other candidate drugs, making the valves (10) of the branch supply path (8b) and branch discharge path (9b) corresponding to the measured section the opened state, making the other valves (10) the closed state, and similarly measuring the channel current, it is possible to measure the effect of a candidate drug on the neuron network. Due to this, high throughput screening of candidate drugs becomes possible.

Measurement of Change of $Ca^{2+}$ Imaging by Administration of Drugs

To show that the results of measurement of the change of the channel current (FIGS. 12(a) to 12(d)) express the healthy state, diseased state due to addition of glutamic acid, and recovered state due to addition of drugs, the $Ca^{2+}$ imaging explained below was performed. Due to $Ca^{2+}$ imaging, it was possible to measure the change of concentration of $Ca^{2+}$ in the cells due to the effects of glutamic acid toxicity.

Inside the 35 mm dish (a), the substrate of FIG. 6 (finished being coated by PLL) was placed. Cerebral cortex cells of a rat on day 17 of birth isolated by the enzyme trypsin were suspended by a commercially available nerve cell medium (Sumitomo Bakelite) to give $2.5 \times 10^5$ cells/ml. This cell suspension: 2 ml (=$5.0 \times 10^5$ cells) was added to the dish (a). In the presence of 5% $CO_2$, this was cultured at 37° C. for 17 days. After formation of the neuron network, this substrate was transferred to another dish (b). To this dish (b), a nerve cell medium (2 ml) was added. To this medium, BAPTA-1 (1 μl) and Cremophor (10 μl) were added and cultured at 37° C. for 1 hour. The culture supernatant was discarded and a buffer solution (145 mM NaCl+10 mM HEPES+8 mM Glucose+3 mM KCl+2 mM $CaCl_2$+1 mM $MgCl_2$, pH7.3): 2 ml was added. This was stored at room temperature away from the light until right before use and the $Ca^{2+}$ fluorescence intensity was measured ($Ca^{2+}$ imaging measurement) (FIG. 13(a)). After this, a buffer solution (500 μl) containing 10 μM concentration glutamic acid was added. After 2.5 minutes, time lapse measurement of $Ca^{2+}$ imaging was started (FIG. 13(b)). After 9.5 minutes, an antagonist mixture: 10 μl containing 2.5 mM D-AP5 and 2.5 mM CNQX was added. Furthermore, after 10.5 minutes, time lapse measurement of $Ca^{2+}$ imaging was performed (FIG. 13(c)).

As one of the pathological conditions of spinal cord injury, Alzheimer's disease, amyotrophic lateral sclerosis (ALS), etc., glutamic acid toxicity is known. FIG. 13(b) shows $Ca^{2+}$ imaging in the case where the neuron network is placed in an environment of glutamic acid toxicity. A state where the concentration of $Ca^{2+}$ in the cells observed by the effects of glutamic acid toxicity rise in a fluctuating manner is observed. On the other hand, FIG. 13(c) means that by adding an antagonist mixed solution, the $Ca^{2+}$ concentration in the cell returns to the state before addition of glutamic acid, that is, a state not affected by toxicity is realized.

The reason $Ca^{2+}$ imaging can be used to detect glutamic acid toxicity is that due to the effects of glutamic acid, the metabotropic receptors become active and the second messenger inositol trisphosphate (IP3) is formed inside the cells. Due to this, the IP3 receptors at the intracellular vesicle surfaces are activated, then the ryanodine receptors (RyR) are activated and the $Ca^{2+}$ concentration in the cell increases. In this process, in some cases, $Ca^{2+}$ vibration occurs. In this cell, due to the increase of $Ca^{2+}$, the frequency of pulsed release (exocytosis) of the neurotransmitter glutamic acid from the presynaptic membrane increases. Due to this, the AMPA receptors or NMDA receptors of the postsynaptic membrane are stimulated and activated and the pulse-like channel current increases. This increase can be eliminated or decreased by addition of the antagonists CNQX and D-AP5 of AMPA receptors or NMDA receptors.

If referring to results of both channel current measurement and $Ca^{2+}$ imaging, it was shown that the effects of glutamic acid toxicity in the case of culture by a glutamic acid-containing medium can be measured by both tests. Furthermore it was shown by both experiments that the effects of glutamic acid toxicity can be suppressed by addition of the AMPA receptor antagonist CNQX and the NMDA receptor antagonist D-AP5. Due to this, it was shown that the results of change of current obtained by channel current measurement using a planar patch clamp device indicate glutamic acid toxicity and easing of glutamic acid toxicity by CNQX and D-AP5. Due to this, it was shown that the composite multi-channel type planar patch clamp device (1b) can be used to enable high throughput screening of drugs easing glutamic acid toxicity.

Further, by performing measurement of the channel current and measurement of $Ca^{2+}$ imaging together in this way, it is possible to understand the conditions of a neuron network more precisely. Further, the channel current wavelength contains extremely abundant information besides what is analyzed in the present embodiment. It is considered that more detailed markers of health, disease, and recovery are provided.

INDUSTRIAL APPLICABILITY

According to the planar patch clamp device of the present invention, it becomes possible to observe the electrical signals at nerve cells at multiple points. This can be used in the field of signal analysis in drug screening or neural networks for nerve cells.

REFERENCE SIGNS LIST 1. single-channel device
1a. multi-channel device
1b. composite multi-channel type patch clamp device
2. electrical insulating substrate
2S. first surface
2S'. second surface
3. through hole
4. cell arrangement region
5. cell
6. first reservoir
6a. main reservoir
6b. branch reservoir
6c. introduction-use liquid passage
6'. second reservoir
7. first electrode part
7'. second electrode part
8. supply path
9. discharge path
8a. main supply path
9a. main discharge path
8b. branch supply path
9b. branch discharge path
10. valve
11. first spacer member
11'. second spacer member
12. first plate member
12'. second plate member
13. lid member
14. electrode container
15. electrode solution
16. Ag/AgCl electrode
17. inorganic porous material
18. electrode pin D, D1 to D4. multi-channel type substrate
P1 to P4. pre-amplifier
M1 to M4. microbranch path plate
19a. main supply path terminal
20a. main discharge path terminal
19b. branch supply path terminal
20b. branch discharge path terminal
21. compressed air line
22. reservoir section
23. partition member
24. cell fixing location
25. protrusion
26. sequencer
27. control PC
28. connection line
29. solenoid valve
30. solenoid valve connection terminal
31. microvalve
32. micropath
33. air pressure pat
34. deformed part

The invention claimed is:

1. A planar patch clamp device comprising:
a first reservoir able to hold a first conductive liquid;
a first electrode part arranged to be able to be electrically conductive with the first reservoir through the first conductive liquid;
a main supply path;
a main discharge path;
a shared electrode part provided in the main supply path or the main discharge path;
an electrical insulating substrate having a plurality of through holes that do not pass cells but are configured to pass liquid from the first reservoir provided at a first surface of the electrical insulating substrate to a second surface opposite the first surface, wherein each through hole is associated with:
    a second reservoir provided at the second surface of the electrical insulating substrate to be able to communicate with a respective through hole of the plurality of through holes and hold a second conductive liquid;
    a branch supply path connected to the second reservoir and configured to supply the second conductive liquid to the second reservoir from the main supply path;
    a branch discharge path connected to the second reservoir and configured to discharge the second conductive liquid from the second reservoir to the main discharge path; and
    at least one nonconductive or insulating valve provided in the branch supply path and/or branch discharge path and disposed between the second reservoir and the shared electrode part, the at least one valve able to allow, when open, or stop, when closed, flow of the second conductive liquid and electrical conduction between the second reservoir and the shared electrode part,
wherein the shared electrode part is arranged to be able to share current with said first electrode part associated with the plurality of through holes.

2. The planar patch clamp device according to claim 1, wherein an electric resistance before and after at least one of the valves is 1 megaohm or more when in a closed configuration.

3. The planar patch clamp device according to claim 1, wherein the planar patch clamp device is a culture-type planar patch clamp device.

4. The planar patch clamp device according to claim 3, wherein an extracellular matrix-forming material is deposited at a rim of at least one through hole on the first surface of the substrate.

5. A planar patch clamp system, comprising:
the planar patch clamp device according to claim 1;
a control part controlling opening and closing of at least one valve of said planar patch clamp device; and
an electrical detecting part configured for detecting an electrical signal at the first electrode part or the shared electrode part of said planar patch clamp device.

6. The planar patch clamp system according to claim 5, further comprising an optical detecting part for detecting an optical signal derived from a cell arranged on said planar patch clamp device.

7. The planar patch clamp device according to claim 1, wherein the at least one nonconductive or insulating valve comprises a micropath formed by an elastic material, a movable valve adjoining the micropath, and a drive system able to drive the movable valve.

8. The planar patch clamp device according to claim 1, wherein the first electrode part or the shared electrode part is a salt bridge type electrode comprising an electrode container filled with a KCl saturated solution, in which an Ag/AgCl electrode is placed, wherein a tip of the electrode container is made of inorganic porous material that is in contact with the first or second conductive liquid.

9. The planar patch clamp device according to claim 1, wherein the at least one nonconductive or insulating valve comprises at least one nonconductive or insulating valve in the branch supply path and at least one nonconductive or insulating valve in the branch discharge path.

* * * * *